US009265405B2

(12) United States Patent  
Okamoto

(10) Patent No.: US 9,265,405 B2  
(45) Date of Patent: Feb. 23, 2016

(54) ENDOSCOPE SYSTEM

(71) Applicant: OLYMPUS CORPORATION, Tokyo (JP)

(72) Inventor: Yasuhiro Okamoto, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 18 days.

(21) Appl. No.: 14/152,319

(22) Filed: Jan. 10, 2014

(65) Prior Publication Data

US 2014/0180008 A1    Jun. 26, 2014

Related U.S. Application Data

(63) Continuation of application No. PCT/JP2013/066733, filed on Jun. 18, 2013.

(30) Foreign Application Priority Data

Jul. 2, 2012   (JP) .................................. 2012-148708

(51) Int. Cl.

| A61B 1/04 | (2006.01) |
|---|---|
| A61B 1/00 | (2006.01) |
| A61B 1/005 | (2006.01) |

(52) U.S. Cl.

CPC ........... *A61B 1/00002* (2013.01); *A61B 1/0016* (2013.01); *A61B 1/0052* (2013.01); *A61B 1/00114* (2013.01); *A61B 1/00119* (2013.01)

(58) Field of Classification Search

CPC ........... A61B 1/00105; A61B 1/00133; A61B 1/00112; A61B 1/00121

USPC ......... 600/132, 114, 126, 139, 141, 145, 146; 604/528; 348/45, 65

See application file for complete search history.

(56) References Cited

U.S. PATENT DOCUMENTS

| 5,243,967 A * | 9/1993 | Hibino .......................... 600/109 |
|---|---|---|
| 6,569,084 B1 | 5/2003 | Mizuno et al. |
| 2009/0209812 A1 | 8/2009 | Omoto |
| 2011/0065994 A1* | 3/2011 | Kudoh et al. ................. 600/146 |
| 2012/0029281 A1* | 2/2012 | Frassica et al. ............... 600/114 |

FOREIGN PATENT DOCUMENTS

| EP | 1 913 862 A1 | 4/2008 |
|---|---|---|
| JP | 05-329097 A | 12/1993 |
| JP | 2000-279367 A | 10/2000 |
| JP | 2005-066128 A | 3/2005 |
| JP | 2009-055956 A | 3/2009 |
| JP | 2009-189653 A | 8/2009 |

OTHER PUBLICATIONS

Extended Supplementary European Search Report dated Aug. 5, 2015 from related European Application No. 13 81 3561.1.

* cited by examiner

*Primary Examiner* — Anhtuan T Nguyen  
*Assistant Examiner* — Timothy J Neal  
(74) *Attorney, Agent, or Firm* — Scully, Scott, Murphy & Presser, PC

(57) ABSTRACT

An insertion portion, a function portion, an operation portion, a universal cord, a connection connector, a drive member that generates a drive force for causing the function portion to act, a connection portion that is provided at the connection connector and has the drive member connected thereto, and a drive force transmitting member that is inserted through the universal cord, and transmits the drive force generated by the drive member connected to the connection portion to the function portion are included.

6 Claims, 17 Drawing Sheets

ENDOSCOPE SYSTEM

CROSS REFERENCE TO RELATED APPLICATION

This application is a continuation application of PCT/JP2013/066733 filed on Jun. 18, 2013 and claims benefit of Japanese Application No. 2012-148708 filed in Japan on Jul. 2, 2012, the entire contents of which are incorporated herein by this reference.

BACKGROUND OF THE INVENTION

1. Field of the Invention

The present invention relates to an endoscope system including an endoscope that is inserted into a subject, a function portion that is provided in the endoscope and is electrically driven, and a control apparatus that performs control of driving the function portion.

2. Description of the Related Art

In recent years, endoscopes having insertion portions that are inserted into subjects have been widely used in a medical field and an industrial field.

An endoscope that is used in the medical field enables observation of an organ in a body cavity and enables various kinds of treatments with use of a treatment instrument inserted into a treatment instrument insertion channel which the endoscope includes, in accordance with necessity, by an elongated insertion portion being inserted into the body cavity that is a subject.

Further, an endoscope that is used in the industrial field enables inspection such as observation of flaws, corrosion and the like of sites to be examined in an object, and various kinds of treatments, by an elongated insertion portion of the endoscope being inserted into the inside of the object such as the inside of a jet engine and piping of a factory.

Here, a configuration is known, in which in an endoscope, a function portion that performs a predetermined action by being electrically driven, for example, a bending portion that bends in a plurality of directions by being electrically driven is provided at an insertion portion.

More specifically, a configuration is known, in which a pulling wire that has a distal end in an insertion direction of the insertion portion (hereinafter, simply called a distal end) connected to the bending portion, and has a proximal end in the insertion direction (hereinafter, simply called a proximal end) wound around a pulley provided in the operation portion, is inserted through the insides of the insertion portion and the operation portion of the endoscope, and a drive member such as a motor that gives a rotational force to the pulley is provided in the operation portion or the like of the endoscope. According to the configuration like this, when operation input is performed from a bending operation member of the operation portion in a state in which the endoscope is connected to an external apparatus, the drive member is driven by power being supplied to the drive member from the external apparatus, and the rotational force is given to the pulley, whereby the pulling wire is pulled and the bending portion is caused to bend.

Further, Japanese Patent Application Laid-Open Publication No. 5-329097 discloses the configuration in which the drive member is provided in the external apparatus of an endoscope, more specifically, the configuration of the endoscope system in which the drive member is provided in the casing of the light source apparatus to which the connector that is provided at the extension end of the universal cord that is extended from the operation portion of the endoscope is connected.

In the endoscope system disclosed in Japanese Patent Application Laid-Open Publication No. 5-329097, when operation input is performed from the bending operation member of the operation portion in the state in which the connector is connected to the light source apparatus, the motor that is a drive member provided in the casing rotates in one direction, the rotational force is given to the pulley via the connector and the rotation transmitting member that is inserted through the inside of the universal cord, and the pulley rotates in one direction. The endoscope system has the configuration in which the pulling wire is pulled to a rear side in the insertion direction of the insertion portion (hereinafter, simply called a rear side) by the above rotation, whereby the bending portion is caused to bend by electric drive.

SUMMARY OF THE INVENTION

An endoscope system in one aspect of the present invention includes an insertion portion that is inserted into a subject, a function portion that is provided at the insertion portion and is capable of acting, an operation portion that is connected to the insertion portion, a universal cord that is extended from the operation portion, and is for connecting to an external apparatus, a connection connector that is provided at an end portion of the universal cord, and is for connecting the universal cord to the external apparatus, a drive member that generates a drive force for causing the function portion to act, a connection portion that is provided at the connection connector, and has the drive member connected thereto, and a drive force transmitting member that is inserted through the universal cord, and transmits the drive force that is generated by the drive member connected to the connection portion to the function portion.

DETAILED DESCRIPTION OF THE PREFERRED EMBODIMENTS

Hereinafter, embodiments of the present invention will be described with reference to the drawings.
(First Embodiment)

Figure 1:
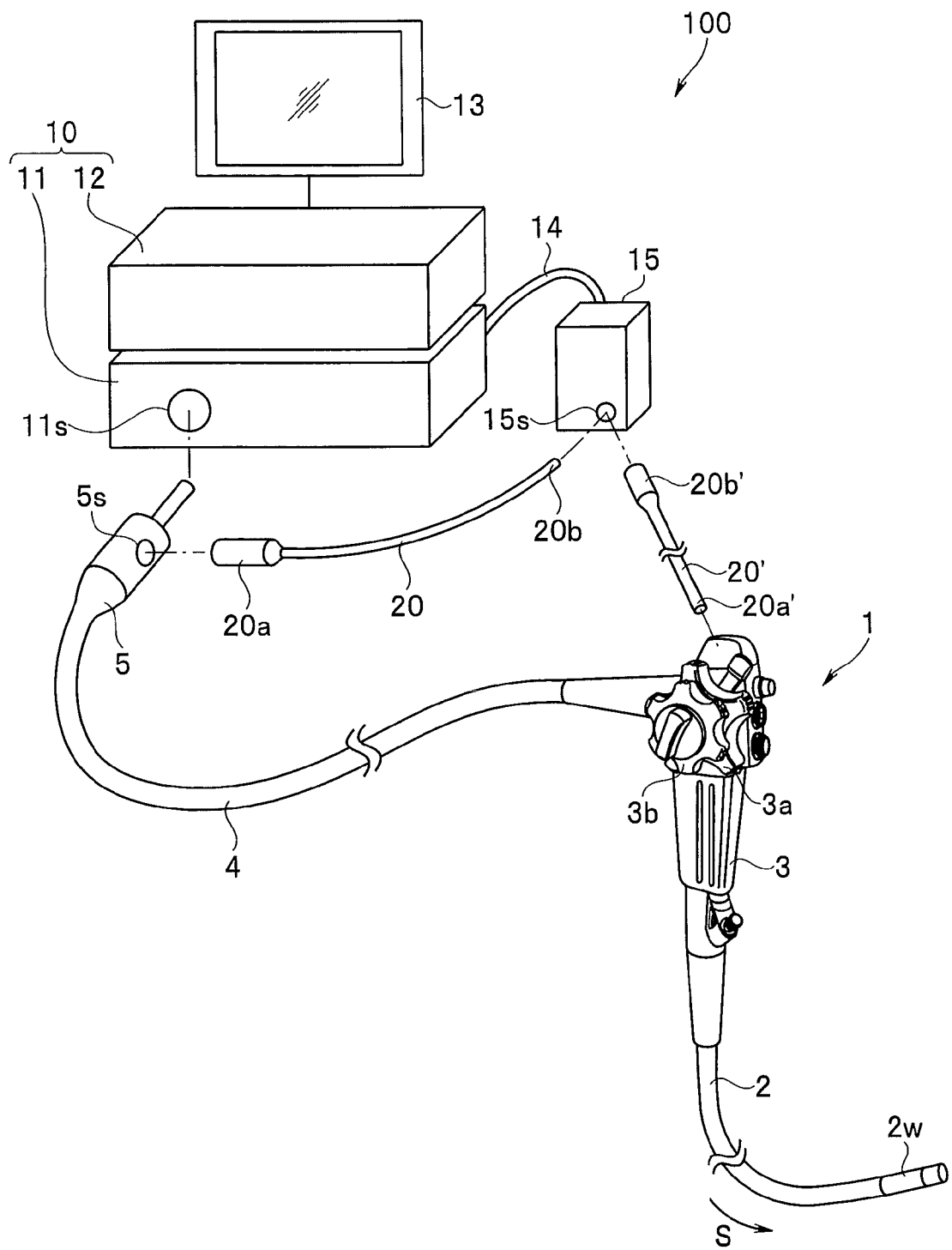
FIG. 1 is a perspective view schematically showing an endoscope system of a first embodiment.

FIG. 1 is a perspective view schematically showing an endoscope system of the present embodiment.

As shown in FIG. 1, an endoscope system 100 has a main part configured by including an endoscope 1 that is inserted into a subject, a display apparatus 10 that is an external apparatus having a light source apparatus 11 and a display processor 12, a monitor 13, and a control apparatus 15 that is an external apparatus.

The endoscope 1 has a main part configured by including an insertion portion 2 that is inserted into a subject and is elongated along an insertion direction S, an operation portion 3 that is connected to a proximal end of the insertion portion 2, and a universal cord 4 that has a connection connector 5 to the light source apparatus 11 at an extension end that is extended from the operation portion 3.

At a distal end side (hereinafter, simply called a distal end side) in the insertion direction S of the insertion portion 2, a bending portion 2w is provided, which is a function portion that bends to, for example, an up, a down, a left and a right, which is a predetermined action, by being electrically driven by being given a drive force from a motor 21 that will be described later.

Further, the operation portion 3 is provided with an up and down bending operation knob 3a that is a rotatable operation member that performs an operation of causing the bending portion 2w to bend, and a left and right bending operation knob 3b that is an operation member.

The connection connector 5 is attachable to and detachable from a connection portion 11s of the light source apparatus 11. Further, an end portion 20a at a connection portion 5s side in a drive cable 20 may be attachable to and detachable from a connection portion 5s that is an attaching and detaching portion of the connection connector 5, with water-tightness. Consequently, the connection portion 5s may be provided with a watertight structure, or a lid may be mounted on the connection portion 5s so that endoscope cleaning can be performed.

Further, an end portion 20b at an opposite side from the end portion 20a of the drive cable 20 is attachable to and detachable from a connection portion 15s of the control apparatus 15. Therefore, the end portion 20b configures an end portion at a connection portion 15s side in the drive cable 20. Further, the end portion 20b also may be attachable to and detachable from the connection portion 15s with water-tightness.

The light source apparatus 11 is electrically connected to the display processor 12 with a connection cable not illustrated, and is electrically connected to the control apparatus 15 via a connection cable 14. Note that the monitor 13 is electrically connected to the display processor 12.

The control apparatus 15 outputs a control signal that performs control of electrically driving the bending portion 2w to the drive cable 20.

Next, an internal configuration of the endoscope system 100 of FIG. 1, more specifically, a configuration that electrically drives the bending portion 2w will be described with use of FIG. 2 and FIG. 3.

Figure 2:
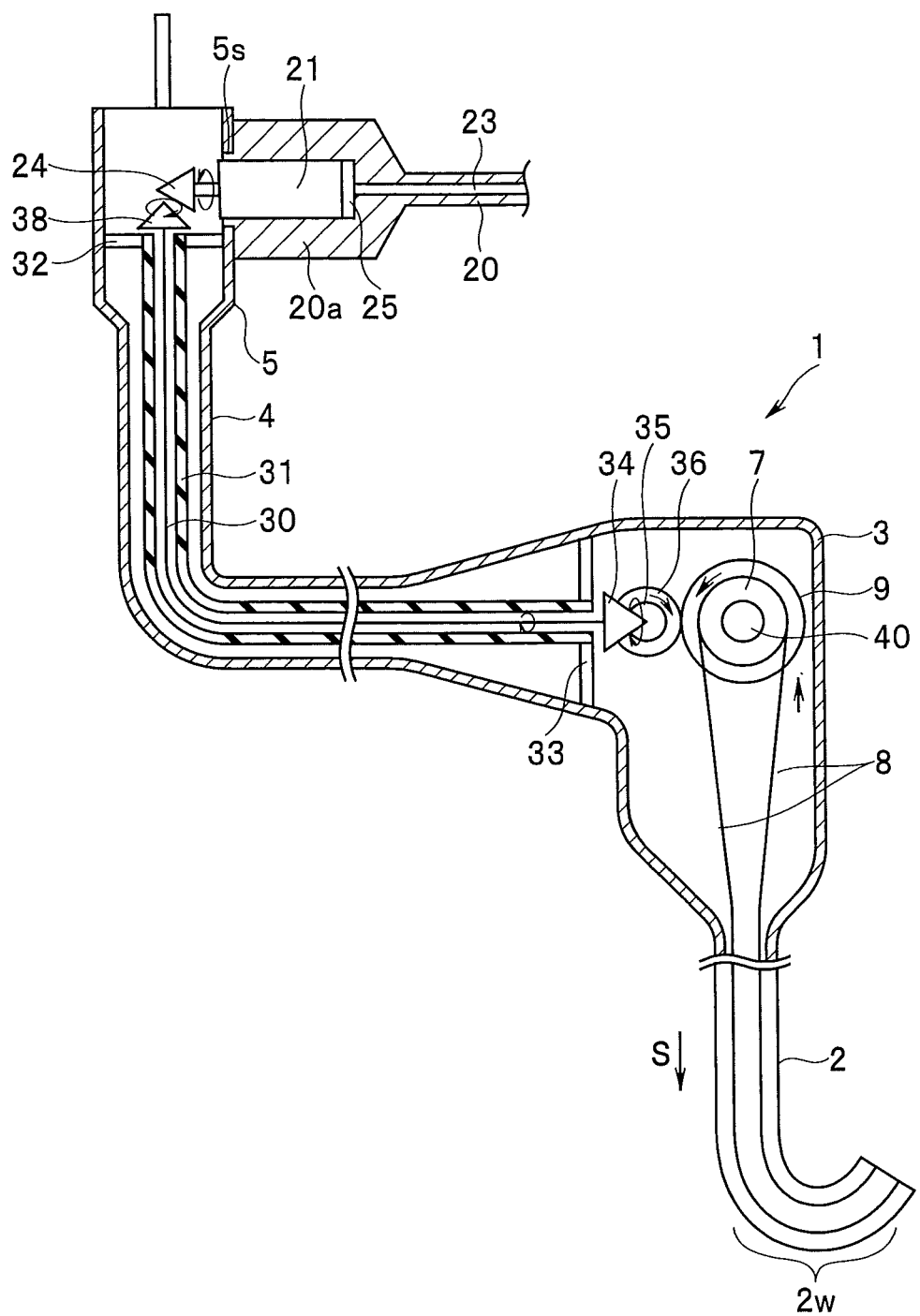
FIG. 2 is a partial sectional view schematically showing only a configuration that electrically drives a bending portion, in an endoscope and part of a drive cable of FIG. 1 by extracting the configuration.

FIG. 2 is a partial sectional view schematically showing only a configuration that electrically drives the bending portion in the endoscope and part of the drive cable of FIG. 1 by extracting the configuration. FIG. 3 is a block diagram schematically showing only the configuration that electrically drives the bending portion in the endoscope system of FIG. 1.

Figure 3:
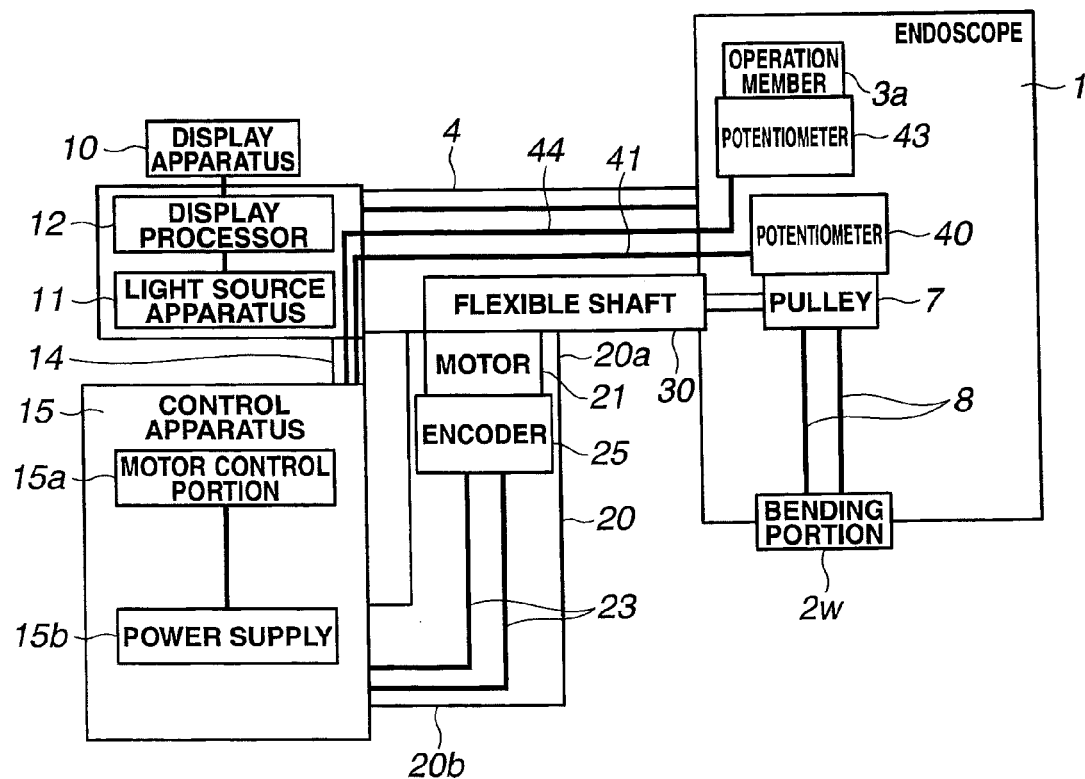
FIG. 3 is a block diagram schematically showing only a configuration that electrically drives the bending portion in the endoscope system of FIG. 1.

Note that in FIG. 2 and FIG. 3, illustration of a configuration that causes the bending portion 2w to bend to the left and the right is omitted in order to simplify the drawings.

As shown in FIG. 2 and FIG. 3, in the operation portion 3, a potentiometer 43 that detects a rotation amount of the up and down bending operation knob 3a, a rotatable pulley 7, and a potentiometer 40 that detects a rotation amount of the pulley 7 are provided.

Note that the potentiometers 40 and 43 are electrically connected to the control apparatus 15 respectively via cables 41 and 44 that are inserted through insides of the universal cord 4, the connection connector 5, the display apparatus 10 and the connection cable 14.

Two wires 8 that have distal ends connected to the bending portion 2w and cause the bending portion 2w to bend in any direction of an up and a down by pulling are respectively inserted through an inside of the insertion portion 2 by being displaced by substantially 180° from each other in a circumferential direction of the insertion portion 2. Further, proximal end sides in the insertion direction S of the two wires 8 (hereinafter, simply called proximal end sides) are wound around the pulley 7.

Further, as shown in FIG. 2, the pulley 7 is rotatable with a spur gear 9 that is provided in the operation portion 3. The spur gear 9 is meshed with a spur gear 36 that is provided in the operation portion 3. Further, the spur gear 36 is meshed with a bevel gear 35 that is provided in the operation portion 3. Further, the bevel gear 35 is meshed with a bevel gear 34 that is provided at an end portion of a flexible shaft 30 that will be described later.

The flexible shaft 30 that is a drive force transmitting member that gives a drive force for bending to the bending portion 2w by rotation is inserted through an inside of the universal cord 4 in a state in which an outer periphery is covered with a tube 31, and in a loosely fitted state so as to be rotatable in the tube 31.

Note that an end portion at the operation portion 3 side, of the tube 31 is fixed to the operation portion 3 with a receiving member 33, and an end portion at the connection connector 5 side is fixed to the connection connector 5 with a receiving member 32.

An end portion at the operation portion 3 side, of the flexible shaft 30 is located by protruding from an end portion of the tube 31 that is fixed with the receiving member 33. Further, the end portion of the flexible shaft 30 is provided with the bevel gear 34 that is rotatable with the flexible shaft 30. Further, an end portion at the connection connector 5 side is also provided with a bevel gear 38 that is rotatable with the flexible shaft 30.

The drive cable 20 is provided with the motor 21 that is a drive member, and an encoder 25 that detects a rotation amount of the motor 21, in an inside of an end portion 20a side, in the drive cable 20.

A cable 23 is extended from the encoder 25. The cable 23 transmits a control signal from a motor control portion 15a in the control apparatus 15 and power from a power supply 15b in the control apparatus 15 to the motor 21 by the end portion 20b of the drive cable 20 being connected to the connection portion 15s of the control apparatus 15.

The motor 21 is driven based on the control signal and the power that are outputted from the control apparatus 15, and gives a drive force for bending to the bending portion 2w via the flexible shaft 30.

More specifically, a rotating shaft of the motor 21 is provided with a bevel gear 24 that rotates with the motor 21. The bevel gear 24 is meshed with the bevel gear 38 that is provided at the end portion of the flexible shaft 30 when the end portion 20a of the drive cable 20 is connected to the connection portion 5s of the connection connector 5. Thereby, the flexible shaft 30 is capable of being given the rotational force from the motor 21 when the drive cable 20 is connected to the connection connector 5.

Thereby, the rotational force of the motor 21 is transmitted to the pulley 7 via the bevel gears 24 and 38, the flexible shaft 30, the bevel gears 34 and 35, and the spur gears 36 and 9, whereby the pulley 7 rotates. As a result, any one of the two wires 8 is pulled, whereby the bending portion 2w is caused to bend in any direction of the up and the down.

Note that the above configuration similarly applies to a configuration that causes the bending portion 2w to bend to the left and the right. Namely, in reality, two wires for bending to the left and the right that are respectively located to differ from the two wires that cause the bending portion 2w to bend in the up and the down directions by substantially 90° in a circumferential direction of the insertion portion 2, and to differ from each other by substantially 180° from each other in the circumferential direction are inserted through the inside of the insertion portion 2. Further, in the operation portion 3, two of the pulleys 7, two of the potentiometers 40 and 43, two of the spur gears 9 and 36 and two of the bevel gears 35 are provided. Further, two of the flexible shafts 30 in which the bevel gears 34 and 38 are provided at the respective end portions are inserted through the inside of the universal cord 4. Further, in the drive cable 20, two of the motors 21, two of the encoders 25 and two of the cables 23 are provided in the drive cable 20.

Next, an operation of the present embodiment will be described.

First, when the up and down bending operation knob 3a is rotationally operated in one direction in order to cause the bending portion 2w to bend in the up direction, for example, in a state in which the end portion 20a of the drive cable 20 is connected to the connection portion 5s of the connection connector 5, and the end portion 20b of the drive cable 20 is connected to the connection portion 15s of the control apparatus 15, a rotation amount is detected by the potentiometer 43, and the detection result is inputted into the control apparatus 15 via the cable 44.

Thereafter, the motor control portion 15a of the control apparatus 15 outputs a control signal to the motor 21 via the cable 23, controls the power supply 15b and outputs power via the cable 23. As a result, the motor 21 rotates in one direction. Note that a rotation amount of the motor 21 is detected by the encoder 25.

Thereafter, a rotational force in the one direction of the motor 21 is transmitted to the pulley 7 via the bevel gears 24 and 38, the flexible shaft 30, the bevel gears 34 and 35 and the spur gears 36 and 9.

As a result, the pulley 7 is rotated in one direction, and thereby the wire 8 for bending in the up direction that is one of the two wires 8 is pulled, whereby the bending portion 2w is caused to bend in the up direction. Namely, the bending portion 2w is electrically caused to bend. Note that the rotation amount of the pulley 7 is detected by the potentiometer 40, and the detection result is inputted into the control apparatus 15 via the cable 41.

Note that bending in the down direction of the bending portion 2w is performed by the wire 8 for bending in the down direction which is the other one of the two wires 8 being pulled, as a result that when the up and down bending operation knob 3a is rotationally operated to the other direction, the motor 21 rotates in the other direction, whereby the rotational force in the other direction of the motor 21 is transmitted to the pulley 7 via the bevel gears 24 and 38, the flexible shaft 30, the bevel gears 34 and 35, and the spur gears 36 and 9, and the pulley 7 rotates in the other direction.

Further, the operation described above similarly applies to a case of performing bending with use of a mechanism not illustrated that causes the bending portion 2w to bend in the left and the right directions and has the same configuration as the mechanism that causes the bending portion 2w to bend in the up and the down directions described above.

Note that by the bending operation knobs 3a and 3b being operated at the same time, the bending portion 2w may be caused to bend in a direction with any one of the up and the down directions and any of the left and the right directions combined.

As above, in the present embodiment, it is shown that the motor 21 which gives the drive force that electrically causes the bending portion 2w to bend to the bending portion 2w by giving the rotational force to the pulley 7 is provided in the drive cable 20.

According to the above, when the motor 21 fails, replacement work of the motor 21 can be easily performed by only replacement of the drive cable 20 which is attachable to and detachable from the endoscope 1 and the control apparatus 15.

Further, since only the motor 21, the encoder 25 and the cable 23 are provided inside the drive cable 20, the replacement work of the motor 21 also can be easily performed by disassembly of the drive cable 20.

Furthermore, for replacement of the motor 21, the endoscope 1, the display apparatus 10 and the control apparatus 15 do not have to be disassembled.

From the above, the endoscope system 100 can be provided, which has the configuration in which the motor 21 which electrically drives the bending portion 2w of the endoscope 1 can be replaced easily with favorable workability.

Note that hereinafter, a modification will be described. In the present embodiment, the configuration is shown, in which the two motors 21 are provided in the drive cable 20 and the bending portion 2w is electrically caused to bend in the up, the down, the left and the right directions.

The configuration is not limited to the above, and may be a configuration in which only the one motor 21 is provided, and, for example, the bending portion 2w is electrically caused to bend only in the up and the down directions by using the motor 21, and is caused to bend in the left and the right directions by the pulley 7 being manually rotated with use of the same configuration as the conventional configuration. As a matter of course, the bending portion 2w may be electrically caused to bend in only the left and the right directions, and may be manually caused to bend in the up and the down directions contrarily to the above.

Further, in the present embodiment, as the operation members that are operated to cause the bending portion 2w to bend, the bending operation knobs 3a and 3b are shown by being cited as examples, but the operation members are not limited to them, and a joystick and a trackball may be adopted.

Figure 4:
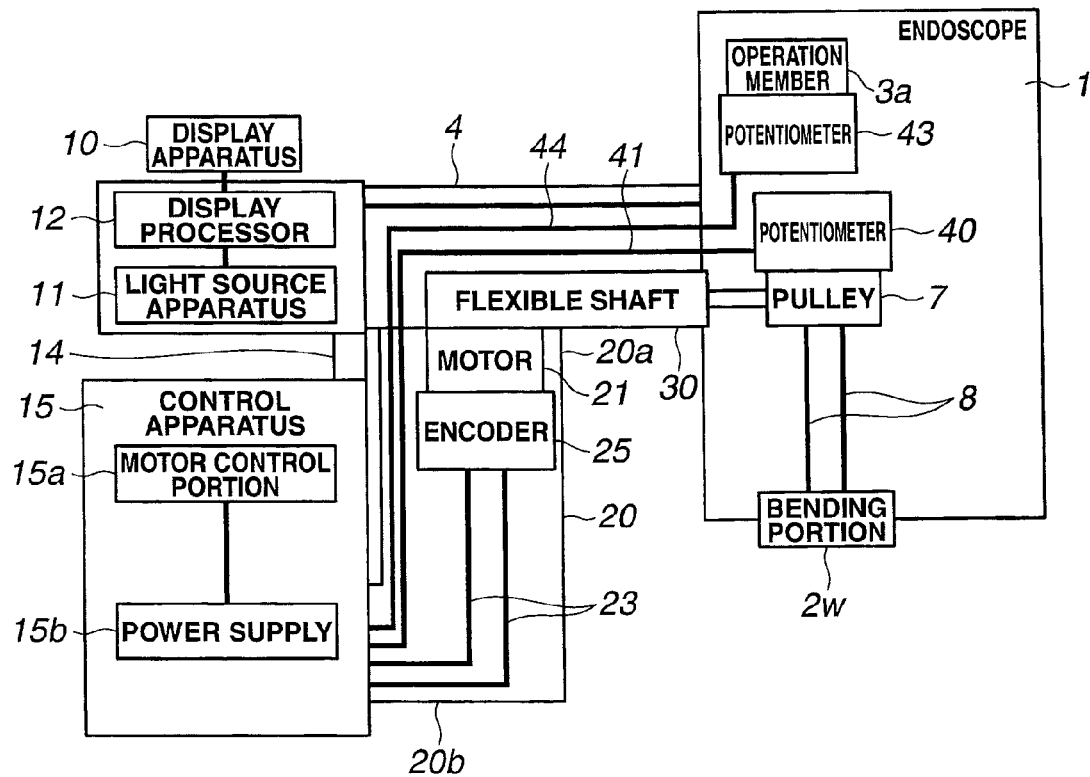
FIG. 4 is a block diagram showing a modification in which cables that are extended from a potentiometer that detects a rotation amount of an operation member and a potentiometer that detects a rotation amount of a pulley are connected to a control apparatus via an inside of a drive cable.

Note that hereinafter, a modification will be shown with use of FIG. 4. FIG. 4 is a block diagram showing the modification in which cables that are extended from a potentiometer that detects a rotation amount of an operation member, and a potentiometer that detects a rotation amount of a pulley are connected to a control apparatus via an inside of a drive cable.

In the present embodiment described above, it is shown that the cables 41 and 44 that are extended from the potentiometers 40 and 43 are electrically connected to the control apparatus 15 via the universal cord 4, the connection connector 5, the display apparatus 10 and the connection cable 14, as shown in FIG. 3.

As a matter of course, the cables 41 and 44 may be electrically connected to the control apparatus 15 via the universal cord 4, the connection connector 5 and an inside of the drive cable 20 as shown in FIG. 4 without being limited to the above.

Figure 5:
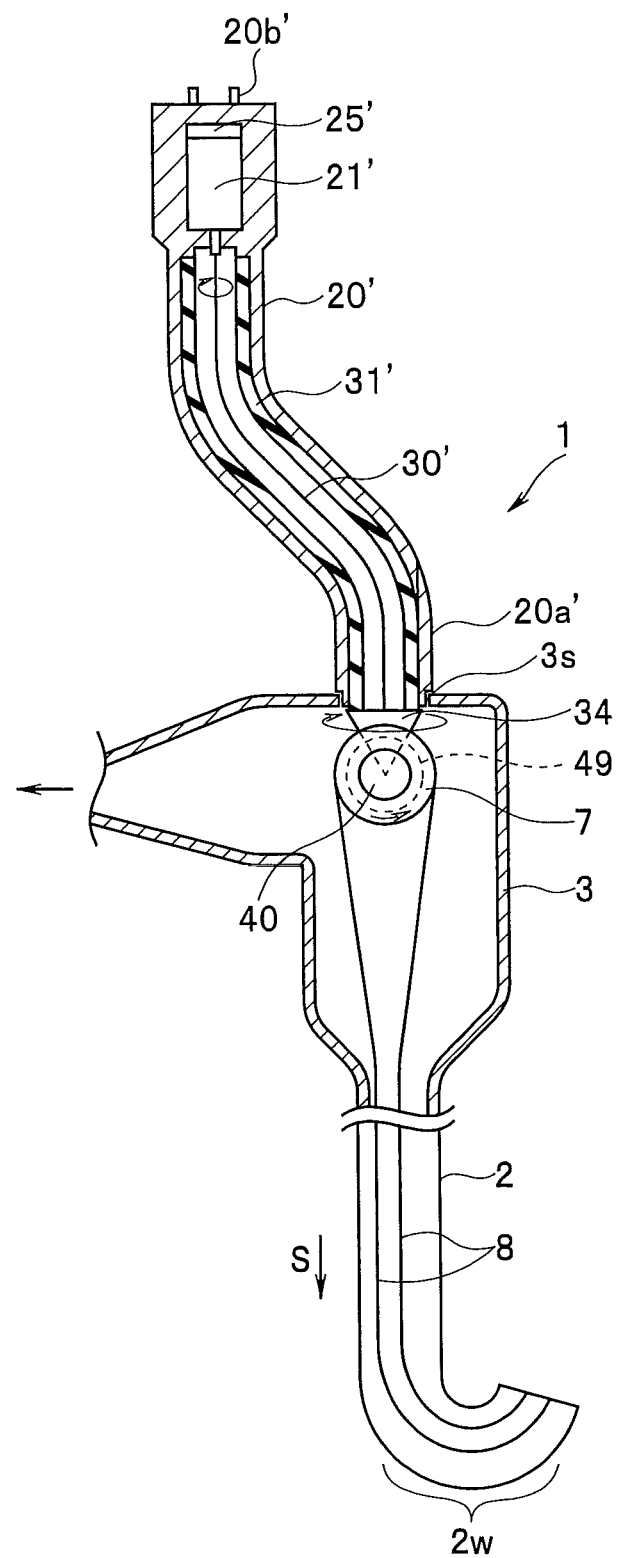
FIG. 5 is a partial sectional view schematically showing only a configuration of a modification that electrically drives the bending portion in part of the endoscope and the drive cable of FIG. 1 by extracting only the configuration.
Figure 6:
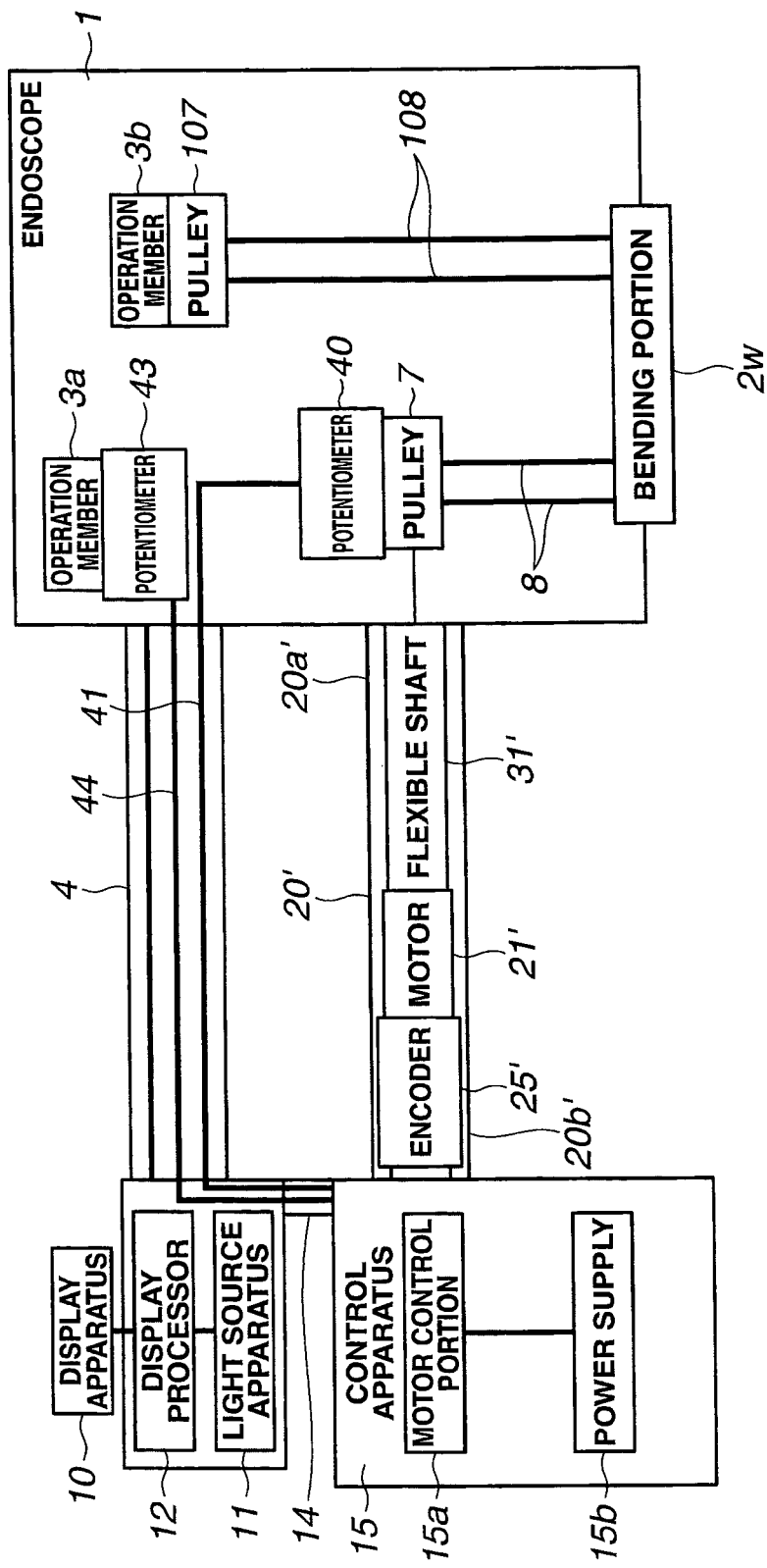
FIG. 6 is a block diagram schematically showing only a configuration of a modification that electrically drives the bending portion in the endoscope system in FIG. 1.

Further, hereinafter, a modification will be shown with use of FIG. 1, FIG. 5 and FIG. 6. FIG. 5 is a partial sectional view schematically showing only a configuration of the modification that electrically drives the bending portion in part of the endoscope and the drive cable of FIG. 1 by extracting the configuration. FIG. 6 is a block diagram schematically showing only the configuration of the modification that electrically drives the bending portion in the endoscope system of FIG. 1.

In the present embodiment described above, it is shown that the end portion 20a of the drive cable 20 in which the end portion 20b is attachable to and detachable from the connection portion 15s of the control apparatus 15 is attachable to and detachable from the connection portion 5s of the connection connector 5 of the endoscope 1.

The end portion is not limited to the above, and as shown in FIG. 1, FIG. 5 and FIG. 6, an end portion 20a' of a drive cable 20' in which an end portion 20b' is attachable to and detachable from the connection portion 15s of the control apparatus 15 may be attachable to and detachable from the connection portion 3s that is an attaching and detaching portion of the operation portion 3 of the endoscope 1. Note that a position of the connection portion 3s is not limited to an upper portion of the operation portion 3, and may be a position where a known treatment instrument insertion channel is provided, for example.

More specifically, in the configuration of the present modification, as shown in FIG. 5 and FIG. 6, the end portion 20a' of the drive cable 20' is attachable to and detachable from the connection portion 3s of the operation portion 3 of the endoscope 1 with water-tightness. Therefore, the connection portion 3s has a watertight structure.

Further, a motor 21' that is a drive member, and an encoder 25' are provided in an inside of an end portion 20b' side, in the drive cable 20'. Further, a flexible shaft 30' that is a drive force transmitting member that is rotatable with rotation of the motor 21' and has an outer periphery covered with a tube 31' are inserted through an inside of the drive cable 20'.

Note that in the configuration of the modification, the flexible shaft 30' is capable of being given a rotational force from the motor 21' in the drive cable 20', and has a function of giving a drive force for bending to the bending portion 2w via the bevel gears 34 and 49 that will be described later, the pulley 7 and the wire 8 by the rotational force, when the drive cable 20 is connected to the connection portion 3s.

Note that functions of the motor 21', the encoder 25', the drive cable 20' and the tube 31' are the same as the functions of the motor 21, the encoder 25, the drive cable 20 and the tube 31' in the present embodiment described above.

The bevel gear 34 is provided at an end portion that protrudes from an end portion of the tube 31' at an opposite side from the motor 21', of the flexible shaft 30', and the bevel gear 34 is meshed with the bevel gear 49 that rotates with the pulley 7.

Therefore, in the configuration shown in FIG. 5 and FIG. 6, the rotational force of the motor 21' is transmitted to the pulley 7 via the flexible shaft 30' and the bevel gears 34 and 49, and thereby the pulley 7 rotates. Thereby, any one of the two wires 8 is pulled, and thereby the bending portion 2w is caused to bend in any direction of the up and the down.

Note that the other operation is the same as that of the present embodiment described above. Further, by the configuration as above, a similar effect to that of the present embodiment can be obtained.

Further, in the configuration shown in FIG. 5 and FIG. 6, the motor 21' and the encoder 25' may be provided in the inside of the end portion 20a' side of the drive cable 20', similarly to the present embodiment.

In the configuration as above, the rotational force of the motor 21' can be directly transmitted to the bevel gear 34 without use of the flexible shaft 30'.

(Second Embodiment)

Figure 7:
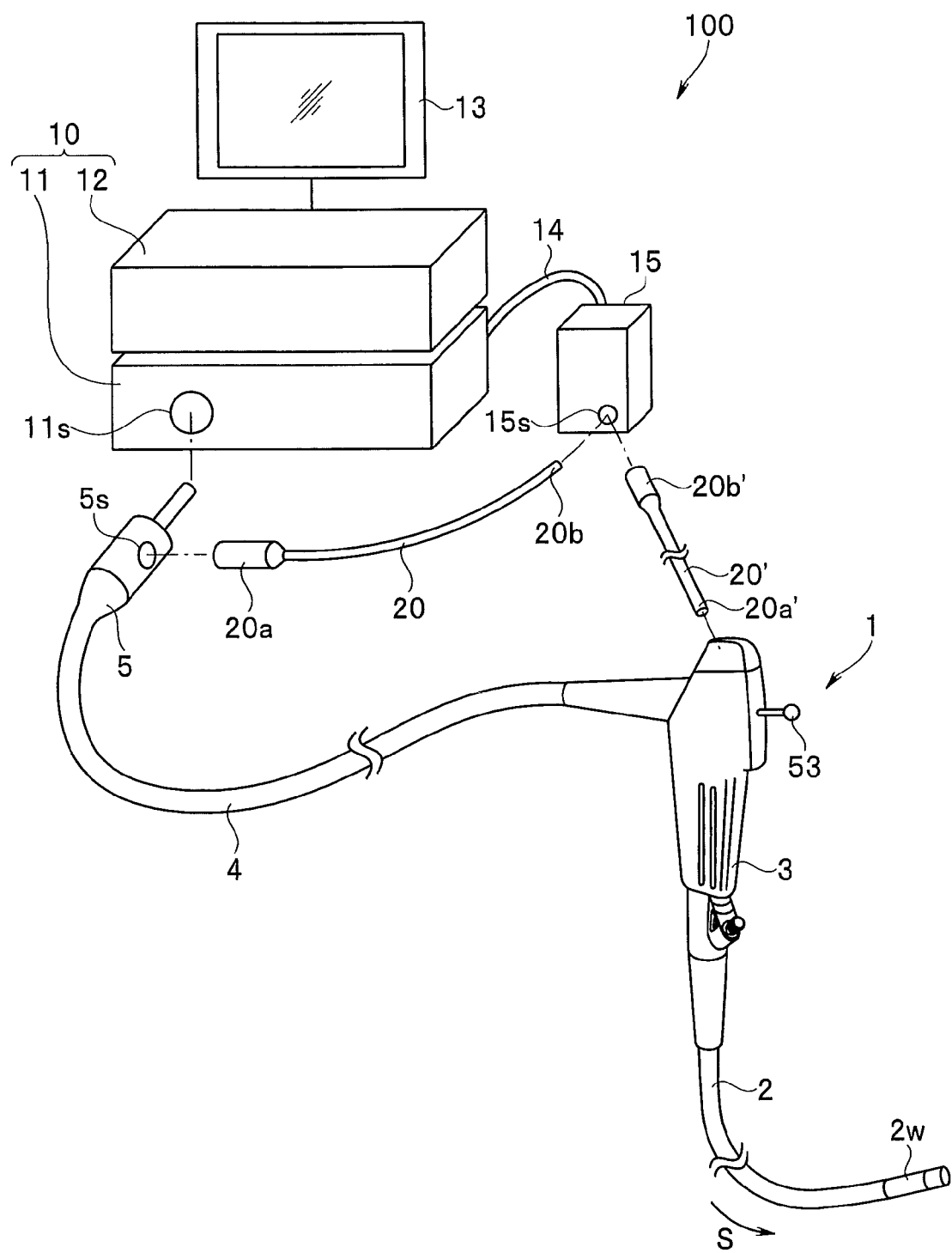
FIG. 7 is a perspective view schematically showing an endoscope system of a second embodiment.
Figure 8:
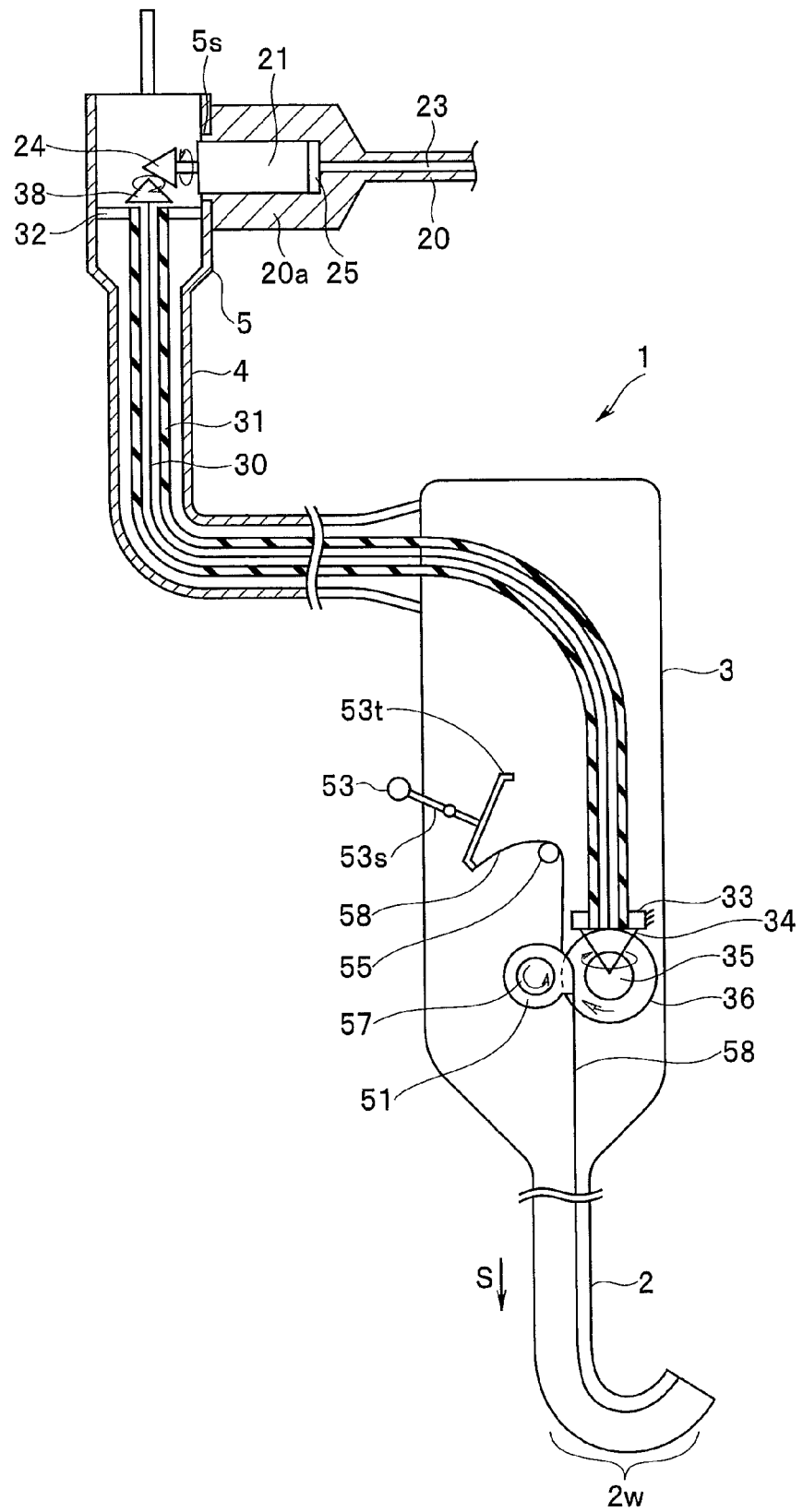
FIG. 8 is a partial sectional view schematically showing only a configuration that electrically drives a bending portion in an endoscope and part of a drive cable of FIG. 7 by extracting the configuration.
Figure 9:
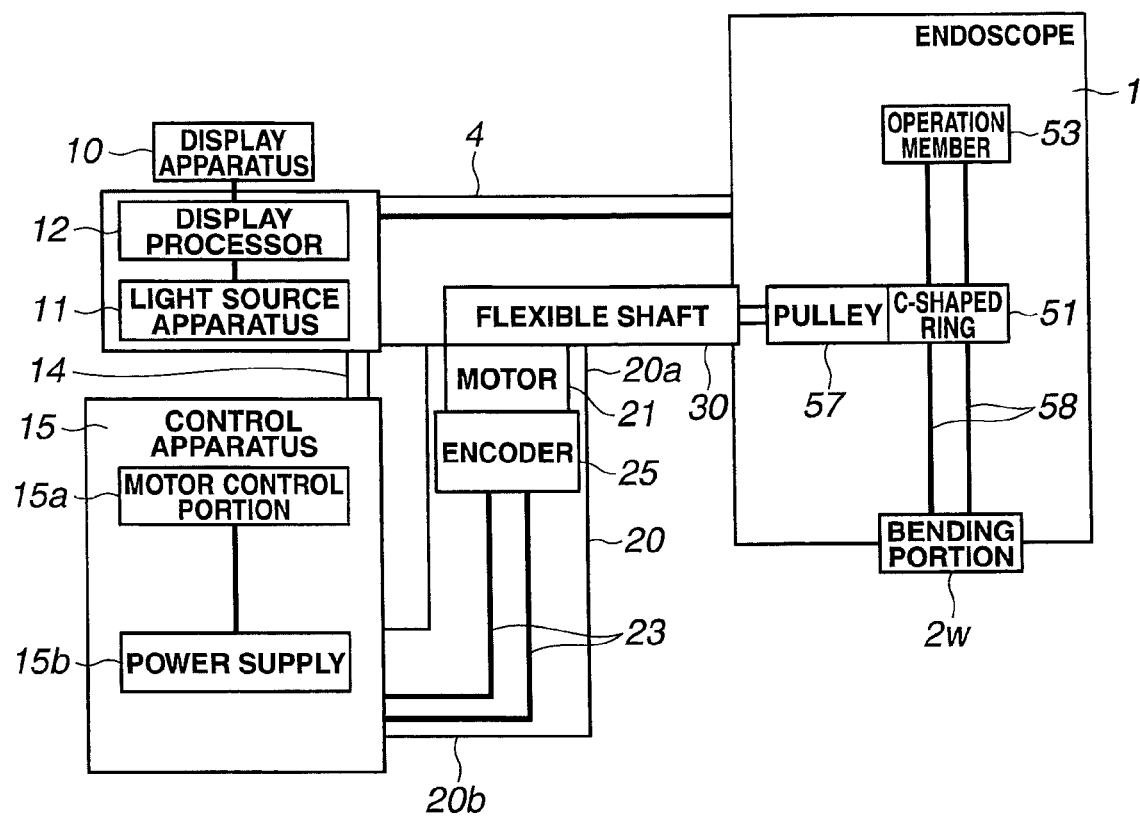
FIG. 9 is a block diagram schematically showing only a configuration that electrically drives the bending portion in the endoscope system of FIG. 7.

FIG. 7 is a perspective view schematically showing an endoscope system of the present embodiment. FIG. 8 is a partial sectional view schematically showing only a configuration that electrically drives a bending portion in an endoscope and a part of a drive cable of FIG. 7 by extracting the configuration. FIG. 9 is a block diagram schematically showing only the configuration that electrically drives the bending portion in the endoscope system of FIG. 7.

A configuration of the endoscope system of the second embodiment differs in that a wire that causes the bending portion to bend is not wound around a pulley, but is wound around a C-shaped ring that is contactable to an outer periphery of the pulley with a frictional force, and is connected to an operation member, as compared with the endoscope system of the first embodiment shown in FIG. 1 to FIG. 3 described above.

Therefore, only the difference will be described, the same components as those in the first embodiment are assigned with the same reference signs, and explanation thereof will be omitted. Note that in FIG. 8 and FIG. 9, illustration of a configuration that causes the bending portion $2w$ to bend in the down direction, and configurations that cause the bending portion $2w$ to bend in the left and the right directions are omitted to simplify the drawings.

As shown in FIG. 7, in the present embodiment, a joystick 53 is used as an operation member that causes the bending portion $2w$ to bend in the up, the down, the left and the right directions, and is provided at the operation portion 3.

As shown in FIG. 8, the joystick 53 is tiltable to the up, the down, the left and the right with a rotation center $53s$ as a center. Further, as shown in FIG. 8 and FIG. 9, a proximal end of a wire 58 for bending in the up direction that has a distal end connected to the bending portion $2w$ is connected to a suspension frame $53t$ of the joystick 53 via a guide roller 55.

An intermediate position of the wire 58 is wound around a C-shaped ring 51 that is provided to be contactable to an outer periphery of a pulley 57, in the operation portion 3.

The C-shaped ring 51 contacts the outer periphery of the pulley 57 with a frictional force by being reduced in diameter by a site between the C-shaped ring 51 and the guide roller 55 in the wire 58 being pulled, with a tilting operation of the joystick 53, and rotates in one direction with the pulley 57, and thereby transmits a pull assisting force that is a rotational force from the pulley 57 to the wire 58 to pull the wire 58.

Note that after the C-shaped ring 51 contacts the outer periphery of the pulley 57, the C-shaped ring 51 does not rotate integrally with the pulley 57, but rotates in the same direction as the pulley 57 while sliding on the outer periphery of the pulley 57.

Further, as shown in FIG. 8, the pulley 57 has a spur gear not illustrated, and the spur gear is meshed with the spur gear 36 that is provided in the operation portion 3. Further, the spur gear 36 is meshed with the bevel gear 35 in the operation portion 3.

Further, in the present embodiment, an end portion of the tube 31 is fixed to a vicinity of the spur gear 36 in the operation portion 3. Namely, an end portion of the flexible shaft 30 is inserted to protrude from the end portion of the tube 31 to about the vicinity of the spur gear 36. Further, the bevel gear 34 that is provided at the end portion of the flexible shaft 30 that is protruded from the end portion of the tube 31 is meshed with the bevel gear 35.

Thereby, the pulley 57 rotates in one direction via the bevel gears 24 and 38, the flexible shaft 30, the bevel gears 34 and 35 and the spur gear 36 with rotation in one direction of the motor 21. Note that in the present embodiment, the pulley 57 always rotates in one direction by drive of the motor 21 when the power supply of the endoscope 1 is on.

Note that in the present embodiment, the potentiometers 40 and 43 and the cables 41 and 44 that are used in the first embodiment described above are not necessary as shown in FIG. 9.

Further, the other configuration is similar to that of the first embodiment described above. Further, the configurations that cause the bending portion $2w$ to bend in the down direction and the left and the right directions are similar to the above. Namely, in reality, in the insertion portion 2, four of the wires 8 are inserted by being displaced by substantially 90° in a circumferential direction of the insertion portion 2, the respective wires 8 are respectively wound around the outer peripheries of four of the C-shaped rings 51 provided in the operation portion 3.

Next, an operation of the present embodiment will be described.

First, when the joystick 53 is operated to tilt in the up direction to cause the bending portion $2w$ to bend in the up direction, for example, in a state in which the end portion $20a$ of the drive cable 20 is connected to the connection portion $5s$ of the connection connector 5, and the end portion $20b$ of the drive cable 20 is connected to the connection portion $15s$ of the control apparatus 15, the wire 8 for bending in the up direction is pulled, and thereby the C-shaped ring 51 for bending in the up direction is reduced in diameter by the wire 8 for bending in the up direction and contacts, with a frictional force, the outer periphery of the pulley 57 that always rotates in one direction via the bevel gears 24 and 38, the flexible shaft 30, the bevel gears 34 and 35 and the spur gear 36 by the motor 21 when the power supply of the endoscope 1 is on.

As a result, the C-shaped ring 51 for bending in the up direction also rotates in the one direction with the pulley 57, and thereby the wire 8 for bending in the up direction is also pulled, whereby the bending portion $2w$ bends in the up direction.

Further, the operation described above similarly applies to the case in which the aforementioned bending portion $2w$ is caused to bend in the down direction and the left and the right directions. Namely, any one or two of the wires 8 that are respectively wound around the four of the C-shaped rings is or are pulled, any one or two of the C-shaped rings 51 is or are reduced in diameter to contact the pulley 57 with a frictional force to rotate in one direction with the pulley 57, whereby the bending portion $2w$ bends in any one direction of the up, the down, the left and the right or a direction with any one of the up and the down directions and any one of the left and the right direction being combined.

In the configuration as above, an effect similar to that of the first embodiment described above can be obtained. Further, in the first embodiment, in order to cause the bending portion $2w$ to bend in the up, the down, the left and the right directions, it is necessary to insert the two flexible shafts 30 through the inside of the universal cord 4, and provide the two pulleys 7 in the operation portion 3, and it is further necessary to provide the two motors 21 in the drive cable 20. However, in the present embodiment, only the single flexible shaft 30, the single motor 21 and the single pulley 57 can be used, and therefore, the configuration that electrically bends the bending portion $2w$ can be simplified more than the first embodiment.

Note that in the present embodiment, it is shown that the operation member is the joystick 53, but the operation member is not limited to the joystick, and an operation knob may be used similarly to the first embodiment as a matter of course.

Further, in the present embodiment, when the bending portion $2w$ is operated to bend, the bending portion $2w$ may be electrically caused to bend, for example, only in the up and the down directions, out of the up, the down, the left and the right, and may be caused to bend in the left and the right directions by a manual operation, or the opposite may be adopted.

Figure 10:
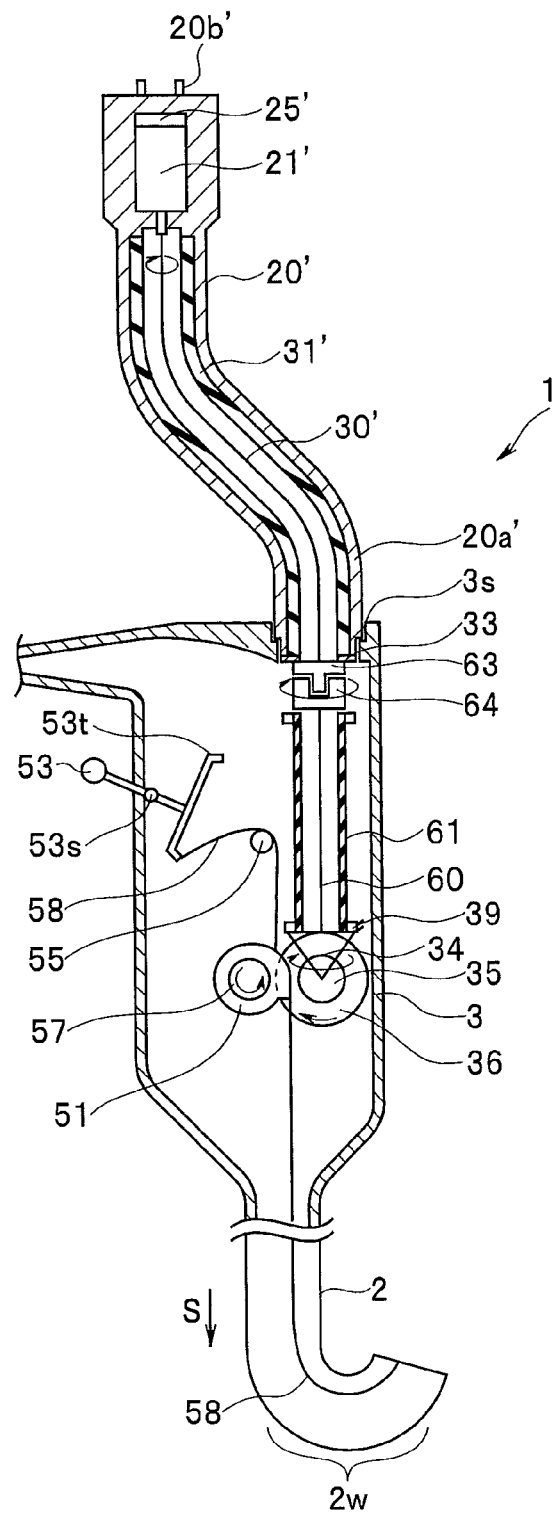
FIG. 10 is a partial sectional view schematically showing only a configuration of a modification that electrically drives the bending portion in part of the endoscope and the drive cable of FIG. 7 by extracting the configuration.
Figure 11:
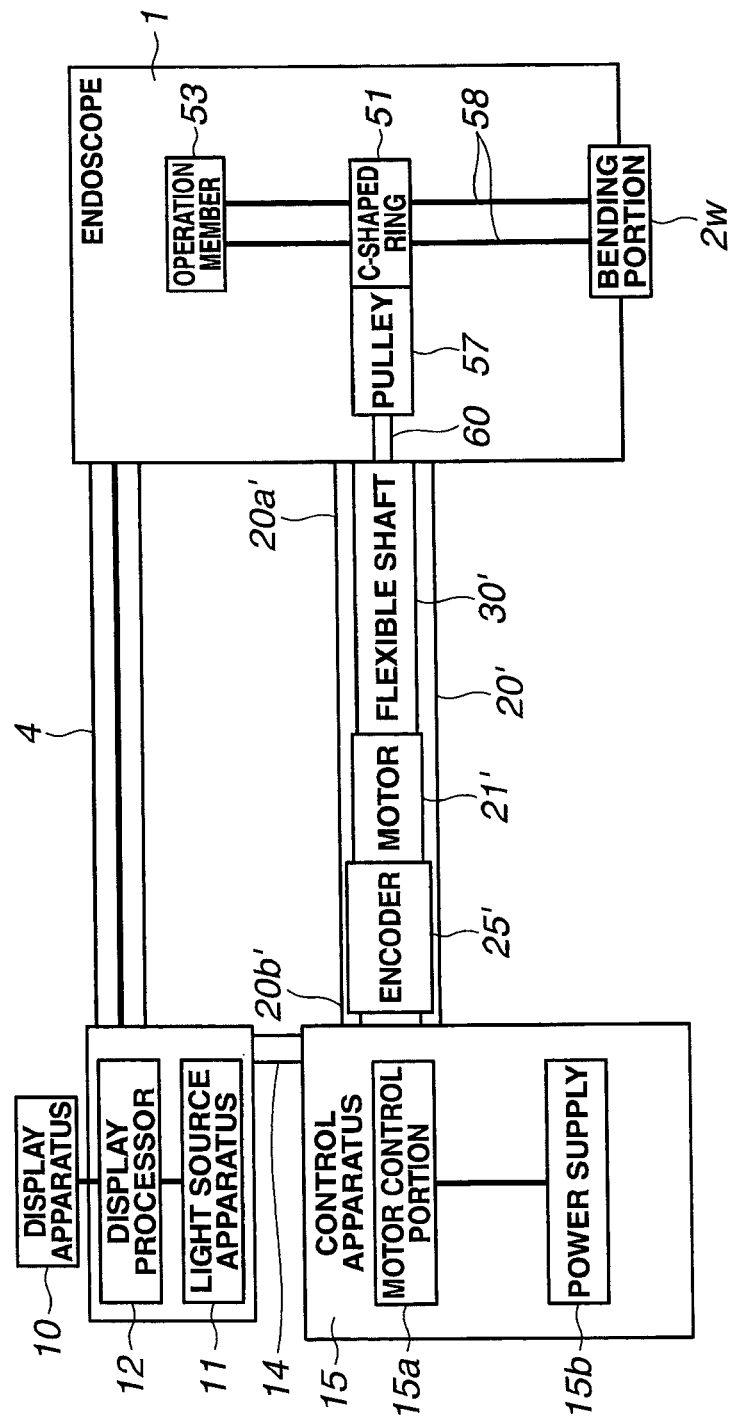
FIG. 11 is a block diagram schematically showing only a configuration of a modification that electrically drives the bending portion in the endoscope system of FIG. 7.

Further, hereinafter, a modification will be shown with use of FIG. 7, FIG. 10 and FIG. 11. FIG. 10 is a partial sectional view schematically showing only a configuration of the modification that electrically drives a bending portion in part of the endoscope and the drive cable of FIG. 7 by extracting the configuration. FIG. 11 is a block diagram schematically showing only the configuration of the modification that electrically drives the bending portion in the endoscope system of FIG. 7.

As shown in FIG. 7, FIG. 10 and FIG. 11, in the present embodiment, the end portion 20a' of the drive cable 20' in which the end portion 20b' is attachable to and detachable from the connection portion 15s of the control apparatus 15 may be attachable to and detachable from the connection portion 3s of the operation portion 3 of the endoscope 1 as shown in FIG. 1, FIG. 5 and FIG. 6 in the first embodiment described above.

Further, in the modification of the present embodiment, the motor 21' that is a drive member, and the encoder 25' are also provided in the inside of the end portion 20b' side, in the drive cable 20'. Further, the flexible shaft 30' that is a drive force transmitting member that is rotatable with rotation of the motor 21' and has an outer periphery covered with the tube 31' is inserted through the inside of the drive cable 20'.

Further, in the configuration of the present modification, as shown in FIG. 10, a drive transmitting member 63 in a convex shape that is engageable with a concave member 64 that is fixed to the inside of the operation portion 3 by the receiving member 33 when the end portion 20a' is connected to the connection portion 3s, and is rotatable with the concave member 64 after being engaged with the concave member 64 is provided at the end portion at the operation portion 3 side, of the flexible shaft 30'. Note that the drive transmitting member 63 and the concave member 64 configure a known coupling (shaft coupling).

In the operation portion 3, a flexible shaft 60 that is a rotatable drive force transmitting member with the concave member 64 provided at one end, and the bevel gear 34 provided at the other end is provided.

Note that in the operation portion 3, an outer periphery of the flexible shaft 60 is covered with a tube 61 with an end portion at the bevel gear 34 side fixed by a receiving member 39 in the operation portion 3.

Note that in the configuration of the present modification, the flexible shaft 30' is capable of being given the rotational force from the motor 21' in the drive cable 20', and when the drive cable 20' is connected to the connection portion 3s, and the drive transmitting member 63 is connected to the concave member 64, the flexible shaft 30' and the flexible shaft 60 have a function of giving a drive force for bending to the bending portion 2w by a rotational force via the bevel gears 34 and 35, the spur gear 36, the pulley 57, the C-shaped ring 51 and the wire 58.

From the above, in the configuration shown in FIG. 10 and FIG. 11, the rotational force in the one direction of the motor 21' is transmitted to the pulley 57 via the flexible shaft 30', the drive transmitting member 63, the concave member 64, the flexible shaft 60, the bevel gears 34 and 35, and the spur gear 36, and thereby the pulley 7 rotates in the one direction.

By the above, by any one or two of the four wires 58 being pulled, any one or two of the four C-shaped rings 51 is or are reduced in diameter, whereby the bending portion 2w is caused to bend in any one direction of the up, the down, the left and the right, or a direction obtained by any one of the up and the down directions and any one of the left and the right directions being combined.

Note that the other operation is the same as that of the present embodiment described above. Further, according to the configuration as above, an effect similar to that of the present embodiment also can be obtained.

Further, in the configuration shown in FIG. 10 and FIG. 11, the motor 21' and the encoder 25' may be provided in the inside of the end portion 20a' side of the drive cable 20' similarly to the present embodiment. In the configuration like this, the rotational force of the motor 21' can be directly transmitted to the drive transmitting member 63 without using the flexible shaft 30'.

Furthermore, in the present embodiment described above, in the inside of the end portion 20b side of the drive cable 20, the motor 21 and the encoder 25 are provided, and a flexible shaft that transmits the rotational force of the motor 21 to the bevel gear 24 may be provided in the drive cable 20, as shown in FIG. 10 and FIG. 11.

(Third Embodiment)

Figure 12:
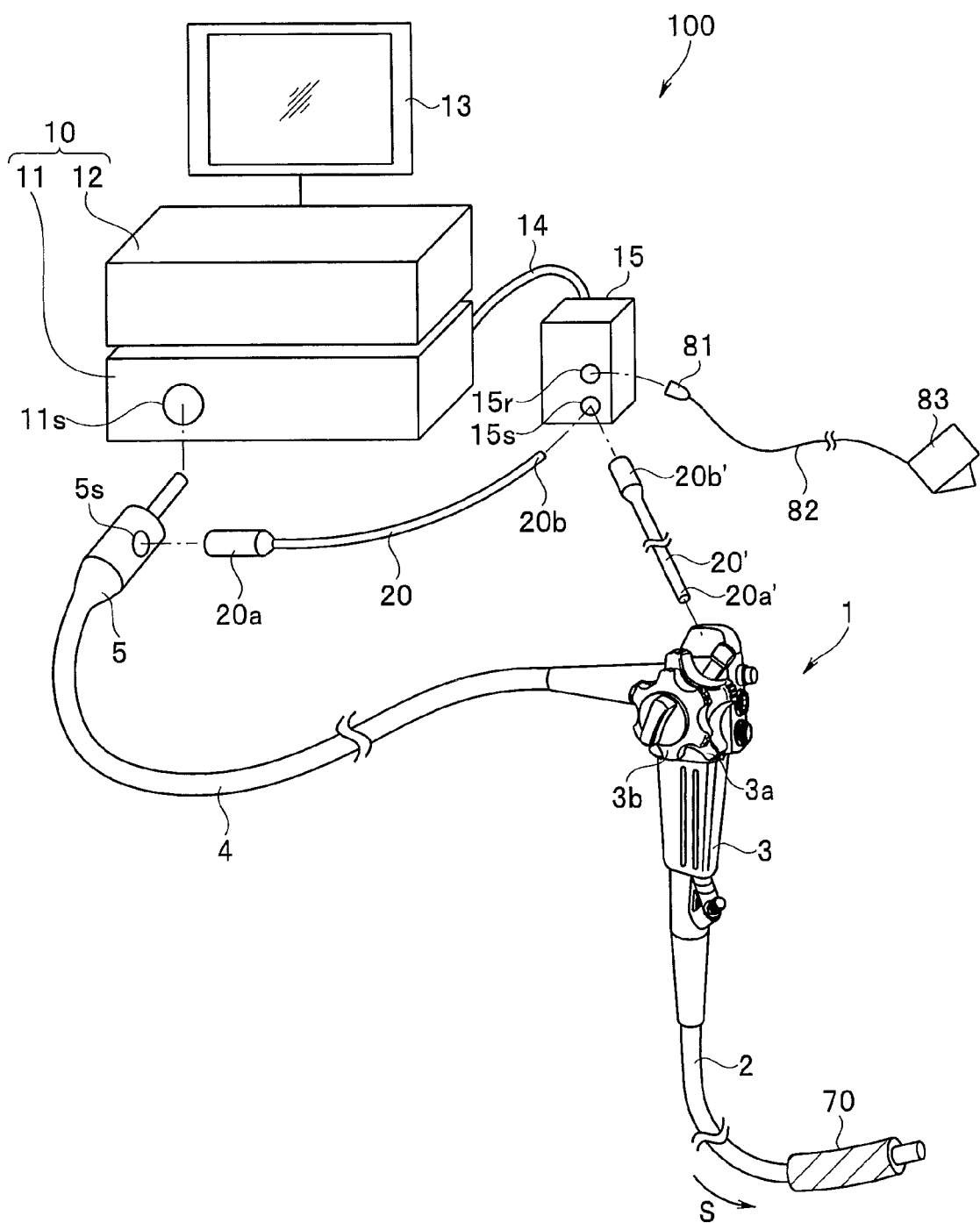
FIG. 12 is a perspective view schematically showing of an endoscope system of a third embodiment.
Figure 13:
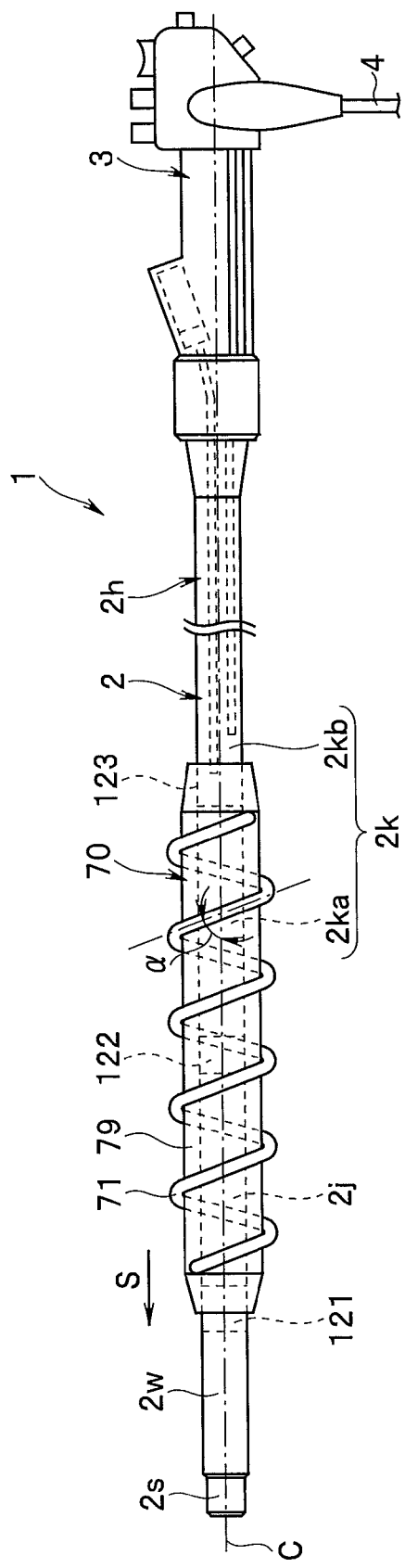
FIG. 13 is a view showing part of a rotary self-propelled endoscope of FIG. 12.
Figure 14:
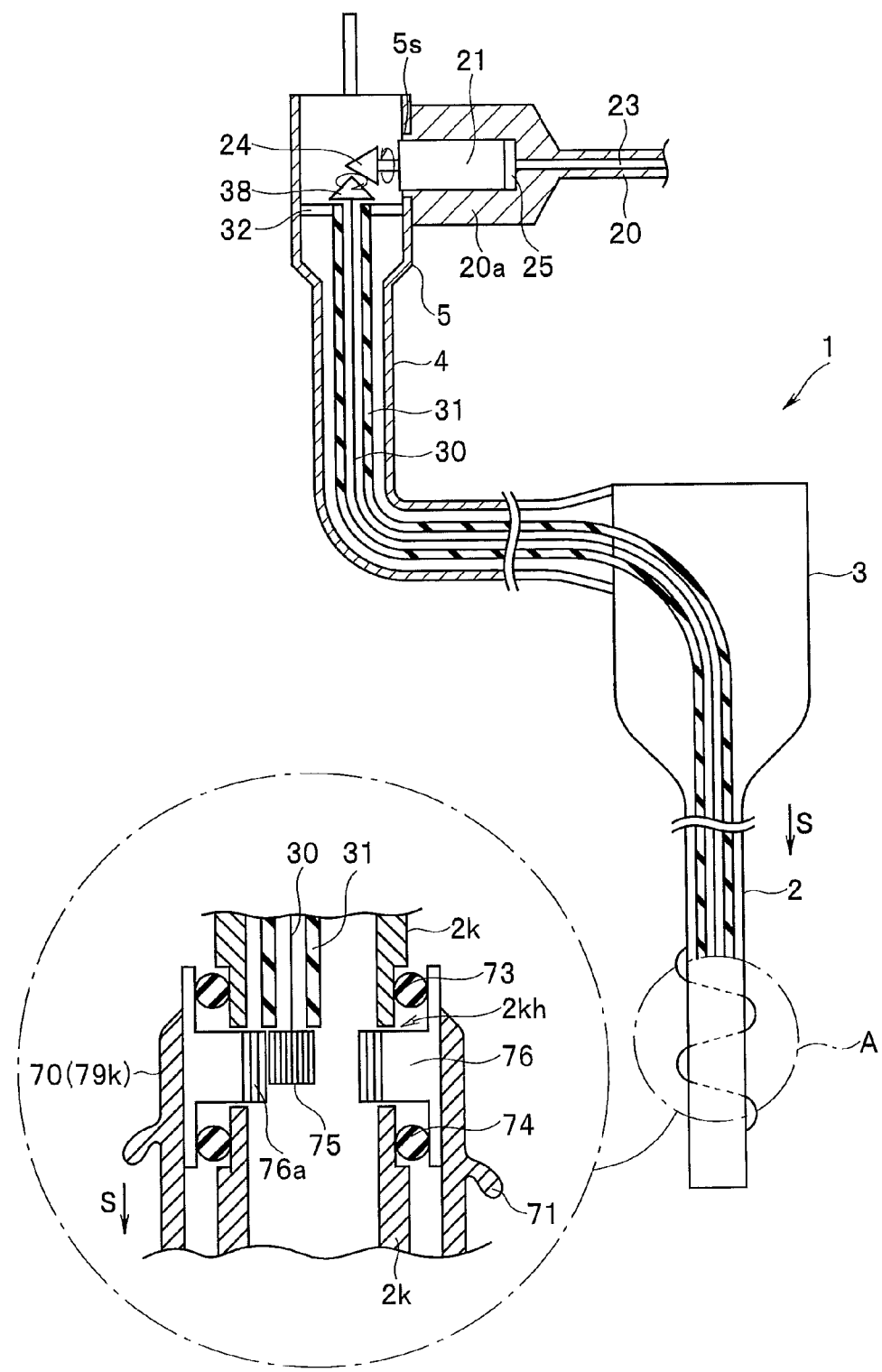
FIG. 14 is a partial sectional view schematically showing only a configuration that electrically drives a bending portion in part of the endoscope and a drive cable of FIG. 12 by extracting the configuration.
Figure 15:
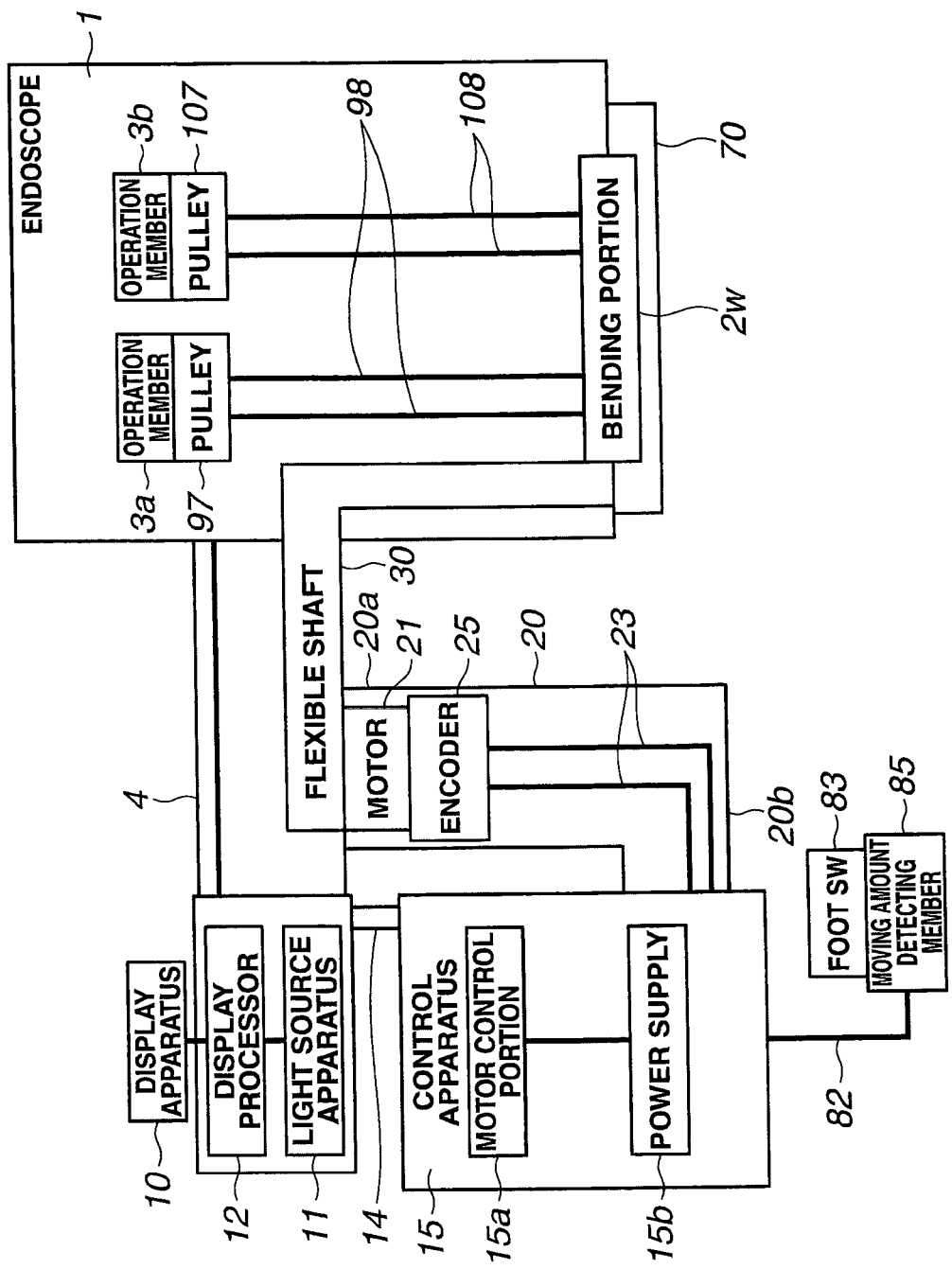
FIG. 15 is a block diagram schematically showing only a configuration that electrically drives the bending portion in the endoscope system of FIG. 12.

FIG. 12 is a perspective view schematically showing an endoscope system of the present embodiment. FIG. 13 is a view showing part of a rotary self-propelled endoscope of FIG. 12. FIG. 14 is a partial sectional view schematically showing only a configuration that electrically drives a bending portion in part of the endoscope and a drive cable of FIG. 12 by extracting the configuration. FIG. 15 is a block diagram schematically showing only the configuration that electrically drives the bending portion in the endoscope system of FIG. 12.

A configuration of the endoscope system of the third embodiment differs in that a function portion that is electrically driven is a rotation portion of the rotary self-propelled endoscope, as compared with the endoscope system of the first embodiment shown in FIG. 1 to FIG. 3 and the endoscope system of the second embodiment shown in FIG. 7 to FIG. 9 that are described above.

Therefore, only the difference will be described, the similar components to those of the first and the second embodiments are assigned with the same reference signs, and explanation thereof will be omitted. Note that in FIG. 12 to FIG. 15, illustration of a detailed configuration that causes the bending portion 2w to bend is omitted to simplify the drawings.

As shown in FIG. 12, in the present embodiment, the endoscope 1 is provided with the up and down bending operation knob 3a and the left and right bending operation knob 3b in the operation portion 3 similarly to the first embodiment.

Further, as shown in FIG. 15, in the operation portion 3, a pulley 97 that is rotationally operated by the up and down bending operation knob 3a, and a pulley 107 that is rotationally operated by the left and right bending operation knob 3b are provided. Further, proximal end sides of two wires 98 for bending to the up and down that have distal ends fixed to the bending portion 2w, and are inserted through the inside of the insertion portion 2 by being displaced by substantially 180° in a circumferential direction of the insertion portion 2 from each other are wound around the pulley 97. Further, proximal end sides of two wires 108 for bending to the left and right that are located by being displaced by substantially 90° in the circumferential direction of the insertion portion 2 with respect to the two wires 98 and located by being displaced by substantially 180° from each other, and have distal ends fixed to the bending portion 2w are wound around the pulley 107.

Therefore, in the present embodiment, such a configuration is adopted that when the up and down bending operation knob 3a is rotationally operated, the pulley 97 rotates, and thereby any one of the two wires 98 is pulled, whereby the bending portion 2w is manually caused to bend in any one direction of the up and the down, whereas when the left and right bending operation knob 3b is rotationally operated, the pulley 107 rotates, and thereby any one of the two wires 108 is pulled, whereby the bending portion 2w is manually caused to bend in any direction of the left and the right.

Note that in the present embodiment, the bending portion 2w also may be caused to bend in a direction obtained by any one direction of the up and the down and any one direction of the left and the right being combined, by both the up and down bending operation knob 3a and the left and right bending operation knob 3b being rotationally operated.

Returning to FIG. 12, an outer periphery of a distal end side of the insertion portion 2 is provided with a rotation body 70 which is a function portion that is put on the outer periphery, electrically rotates by being given a drive force from the motor 21, and enhances insertability of the insertion portion 2 in a subject.

Namely, the endoscope 1 that is used in the present embodiment is configured by a known rotary self-propelled endoscope. The configuration of the rotary self-propelled endoscope will be briefly described with use of FIG. 13.

As shown in FIG. 13, the insertion portion 2 has an insertion portion main body 2h elongated along the insertion direction S.

The insertion portion main body 2h has a distal end rigid portion 2s that is located at the most distal end portion, an active bending portion 2w that is located at a more proximal end side than the distal end rigid portion 2s, a passive bending portion 2j that is located at a more proximal end side than the active bending portion 2w, and passively bends by receiving an external force, and a corrugated tube portion 2k that is located at a more proximal end side than the passive bending portion 2j.

Note that the corrugated tube portion 2k is configured by a first corrugated tube portion 2ka that is located at the distal end side, and a second corrugated tube portion 2kb that is connected to a proximal end of the second corrugated tube portion 2ka via a corrugated tube connecting portion 123. Further, the active bending portion 2w and the passive bending portion 2j are connected by a relay connection portion 122.

Outer peripheries of the passive bending portion 2j and the first corrugated tube portion 2ka of the insertion portion 2 are covered with the rotation body 70 so that the rotation body 70 is rotatable around a longitudinal axis C.

The rotation body 70 has a tube main body 79, and a fin portion 71 that is wound around an outer periphery of the tube main body 79 in a spiral shape along the insertion direction S.

The fin portion 71 protrudes outward in a radial direction of the tube main body 79 from the tube main body 79. Further, the fin portion 71 is wound in a spiral shape with an angle α relative to the longitudinal axis C being an angle larger than 45°, for example.

The rotation body 70 gives a propelling force to the insertion portion 2 by a screw action with a body cavity wall by the fin portion 71 contacting the body cavity wall with rotation.

Next, a configuration that rotates the rotation body 70 will be described with use of FIG. 12, FIG. 14 and FIG. 15.

As shown in FIG. 14, in the present embodiment, the distal end of the tube 31 is located by being extended into the insertion portion 2, similarly to the second embodiment. Further, at an end portion of the flexible shaft 30 that is rotatably inserted in the inside of the tube 31, a gear 75 that is located to protrude forward in the insertion direction S (hereinafter, simply called forward) from the distal end of the tube 31 is provided rotatably with the flexible shaft 30, as shown by being enlarged in A in FIG. 14.

Further, as shown by being enlarged in A in FIG. 14, in the corrugated tube portion 2k, a through-hole 2kh that penetrates in the radial direction is formed.

Furthermore, a gear member 76 that has a gear 76a at an inward flange portion is fixed to an inner periphery of a proximal end side of the rotation body 70, and the gear 76a is meshed with the gear 75 by being protruded into the corrugated tube portion 2k via the through-hole 2kh.

Further, as shown by being enlarged in A in FIG. 14, a site of the gear member 76 except for the inward flange portion provided with the gear 76a is in contact with an outer periphery of the corrugated tube portion 2k rotatably via O-shaped rings 73 and 74. The O-shaped rings 73 and 74 are members that prevent a liquid from entering an inside of the corrugated tube portion 2k via the through-hole 2kh from an outside.

Therefore, the configuration is such that when the flexible shaft 30 rotates with rotation of the motor 21, the gear 76a that is meshed with the gear 75 rotates, and the rotation body 70 to which the gear member 76 is fixed rotates.

Note that a configuration that rotates the flexible shaft 30 is the same as the configuration shown in FIG. 8 in the second embodiment described above.

Further, as shown in FIG. 12 and FIG. 15, in the present embodiment, a connector 81 of a cable 82 that is extended from a foot switch 83 is attachable to and detachable from a connection portion 15r that is different from the connection portion 15s of the control apparatus 15.

The foot switch 83 is a switch that instructs the control apparatus 15 to drive of the motor 21, and the control apparatus 15 controls a drive amount of the motor 21 in accordance with an action amount of the foot switch 83 that is detected by a moving amount detecting member 85, as shown in FIG. 15.

Next, an operation of the present embodiment will be described.

First, when the foot switch 83 is pressed down to rotate the rotation body 70 in a state in which the end portion 20a of the drive cable 20 is connected to the connection portion 5s of the connection connector 5, while the end portion 20b of the drive cable 20 is connected to the connection portion 15s of the control apparatus 15, and further, the connector 81 of the cable 82 that is extended from the foot switch 83 is connected to the connection portion 15r of the control apparatus 15, a moving amount of the foot switch 83, namely, a pressed amount is detected by the moving amount detecting member 85, and the detection result is transmitted to the control apparatus 15 via the cable 82.

Thereafter, the motor control portion 15a of the control apparatus 15 outputs a control signal to the motor 21 via the cable 23 in accordance with the moving amount of the foot switch 83, controls the power supply 15b and outputs power via the cable 23.

As a result, the motor 21 rotates in one direction or in the other direction. Note that the rotation amount of the motor 21 is detected by the encoder 25. Further, the direction in which the motor 21 rotates can be switched by two switches being provided at the foot switch 83.

Thereafter, the rotational force of the motor 21 is transmitted to the rotation body 70 via the bevel gears 24 and 38, the flexible shaft 30 and the gears 75 and 76a. As a result, the rotation body 70 rotates.

As above, even with the configuration that rotates the rotation body 70 by using the motor 21, the motor 21 is provided in the drive cable 20, and therefore, if the motor 21 fails, replacement work of the motor 21 can be easily performed by only replacement of the drive cable 20 that is attachable to and detachable from the endoscope 1 and the control apparatus 15.

Further, only the motor 21, the encoder 25 and the cable 23 are provided in the drive cable 20, and therefore, replacement work of the motor 21 also can be easily performed by disassembly of the drive cable 20.

Furthermore, for replacement of the motor 21, it is not necessary to disassemble the endoscope 1, the display apparatus 10 and the control apparatus 15.

From the above, the endoscope system 100 can be provided, which has the configuration that can replace the motor 21 that electrically drives the rotation body 70 of the endoscope 1 easily with favorable workability.

Note that in the present embodiment described above, it is shown that the bending portion 2w is manually caused to bend by the bending operation knobs 3a and 3b. The present invention is not limited to the above, and the bending portion 2w may be electrically caused to bend with use of the configurations of the first and the second embodiments described above, as a matter of course.

Figure 16:
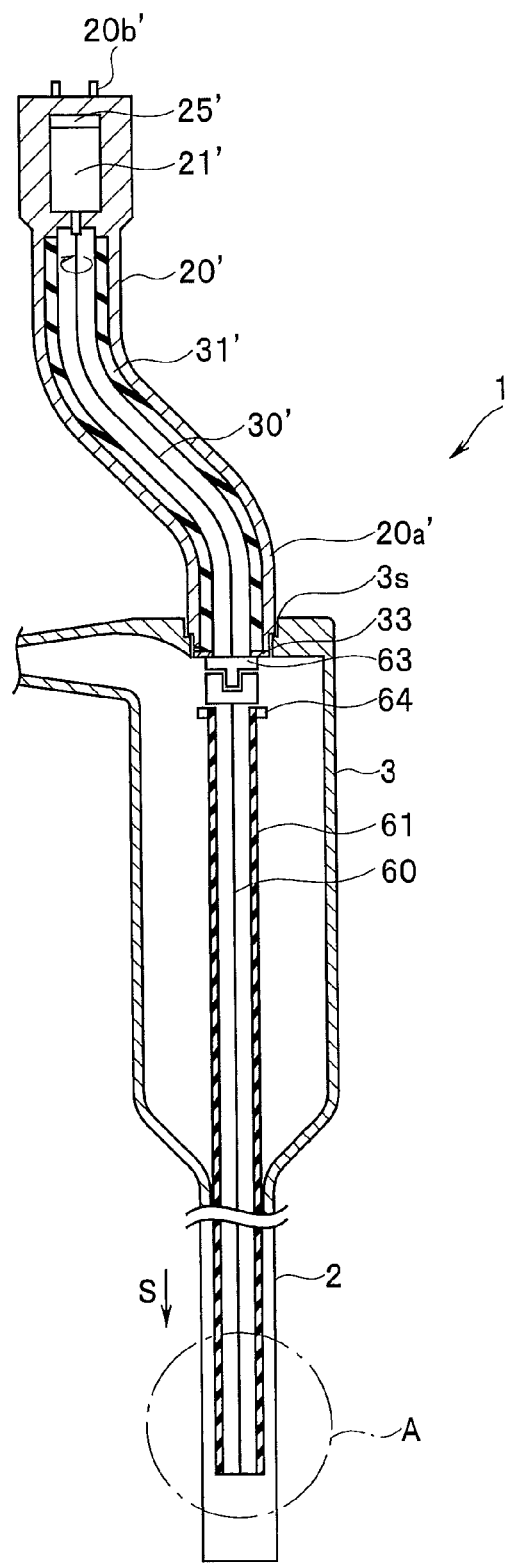
FIG. 16 is a partial sectional view schematically showing only a configuration of a modification that electrically drives the bending portion in part of the endoscope and the drive cable of FIG. 12 by extracting the configuration.
Figure 17:
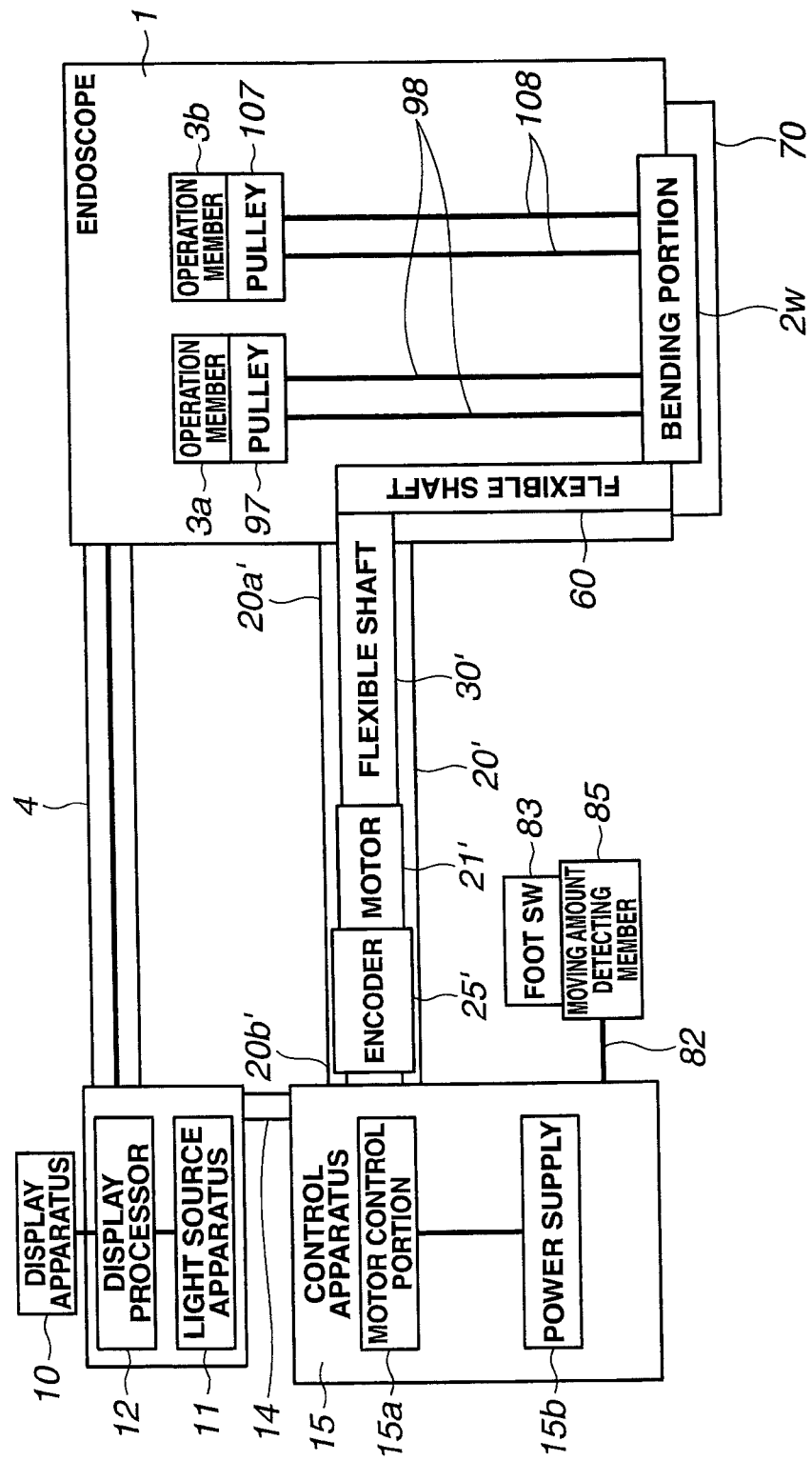
FIG. 17 is a block diagram schematically showing only a configuration of a modification that electrically drives the bending portion in the endoscope system of FIG. 12.

Note that hereinafter, a modification will be shown with use of FIG. 12, FIG. 16 and FIG. 17. FIG. 16 is a partial sectional view schematically showing only a configuration of the modification that electrically drives a bending portion in a part of the endoscope and the drive cable of FIG. 12 by extracting the configuration. FIG. 17 is a block diagram schematically showing only the configuration of the modification that electrically drives the bending portion in the endoscope system of FIG. 12.

As shown in FIG. 12, FIG. 16 and FIG. 17, in the present embodiment, the end portion 20a' of the drive cable 20' in which the end portion 20b' is attachable to and detachable from the connection portion 15s of the control apparatus 15 may be also attachable to and detachable from the connection portion 3s of the operation portion 3 of the endoscope 1 similarly to FIG. 1, FIG. 5 and FIG. 6 of the first embodiment.

Namely, in the modification of the present embodiment, the motor 21' that is a drive member, and the encoder 25' are also provided in the inside of the end portion 20b' side, in the drive cable 20'. Further, the flexible shaft 30' that is a drive force transmitting member that is rotatable with rotation of the motor 21' and has the outer periphery covered with the tube 31' is inserted through the inside of the drive cable 20'.

Further, in the configuration of the present modification, the end portion at the operation portion 3 side, of the flexible shaft 30' is provided with the drive transmitting member 63 in the convex shape that is engageable with the concave member 64 that is fixed to the inside of the operation portion 3 by the receiving member 33, and is rotatable with the concave member 64 after being engaged with the concave member 64 when the end portion 20a' is connected to the connection portion 3s.

In the operation portion 3, the flexible shaft 60 that is a rotatable drive force transmitting portion in which the concave member 64 is provided at one end and the gear 75 is provided at the other end as shown by being enlarged in A in FIG. 14 is provided. Note that in the operation portion 3, an outer periphery of the flexible shaft 60 is covered with a tube 61.

Note that in the configuration of the present modification, the flexible shaft 30' is capable of being given the rotational force from the motor 21' in the drive cable 20', and the flexible shaft 30' and the flexible shaft 60 have a function of giving the rotational force to the rotation body 70 via the gears 75 and 76a when the drive cable 20' is connected to the connection portion 3s, and the drive transmitting member 63 is connected to the concave member 64.

Further, a configuration of a site enclosed by A of FIG. 16 is the same as the configuration that is shown by being enlarged in A in FIG. 14, and therefore, explanation thereof will be omitted.

From the above, in the configuration shown in FIG. 16 and FIG. 17, the rotational force of the motor 21' is transmitted to the rotation body 70 via the flexible shaft 30', the drive transmitting member 63, the concave member 64, the flexible shaft 60, and the gears 75 and 76a, and thereby the rotation body 70 is rotated. Note that the other operation is the same as that of the present embodiment described above. Further, by the configuration as above, a similar effect to that of the present embodiment also can be obtained.

Further, in the configuration shown in FIG. 16 and FIG. 17, the motor 21' and the encoder 25' may be provided in the inside of the end portion 20a' side, of the drive cable 20', similarly to the present embodiment. In the configuration like this, the rotational force of the motor 21' can be transmitted directly to the drive transmitting member 63 without use of the flexible shaft 30'.

Further, in the present embodiment described above, as shown in FIG. 16 and FIG. 17, in the inside of the end portion 20b side of the drive cable 20, the motor 21 and the encoder 25 are provided, and a flexible shaft that transmits the rotational force of the motor 21 to the bevel gear 24 may be provided in the drive cable 20.

Note that in the first to the third embodiments described above, the example in which the display processor 12, the light source apparatus 11 and the control apparatus 15 are provided separately is cited and shown. But the present invention is not limited to the example, and the display processor 12, the light source apparatus 11 and the control apparatus 15 may be integrally formed. Further, only the display processor 12 and the light source apparatus 11 may be integrally formed. Further, only the light source apparatus 11 and the control apparatus 15 may be integrally formed. Furthermore, only the display processor 12 and the control apparatus 15 may be integrally formed.

Figure 18:
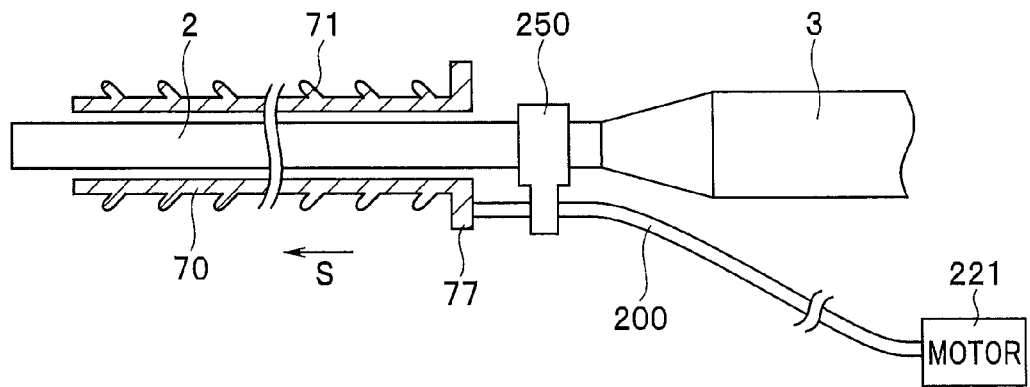
FIG. 18 is a view schematically showing a configuration that connects a cover sheath that has a flexible shaft that supplies a rotational force to a rotation body that is put on an outer periphery of an insertion portion of an endoscope inserted through an inside thereof, and the insertion portion with a clip.
Figure 19:
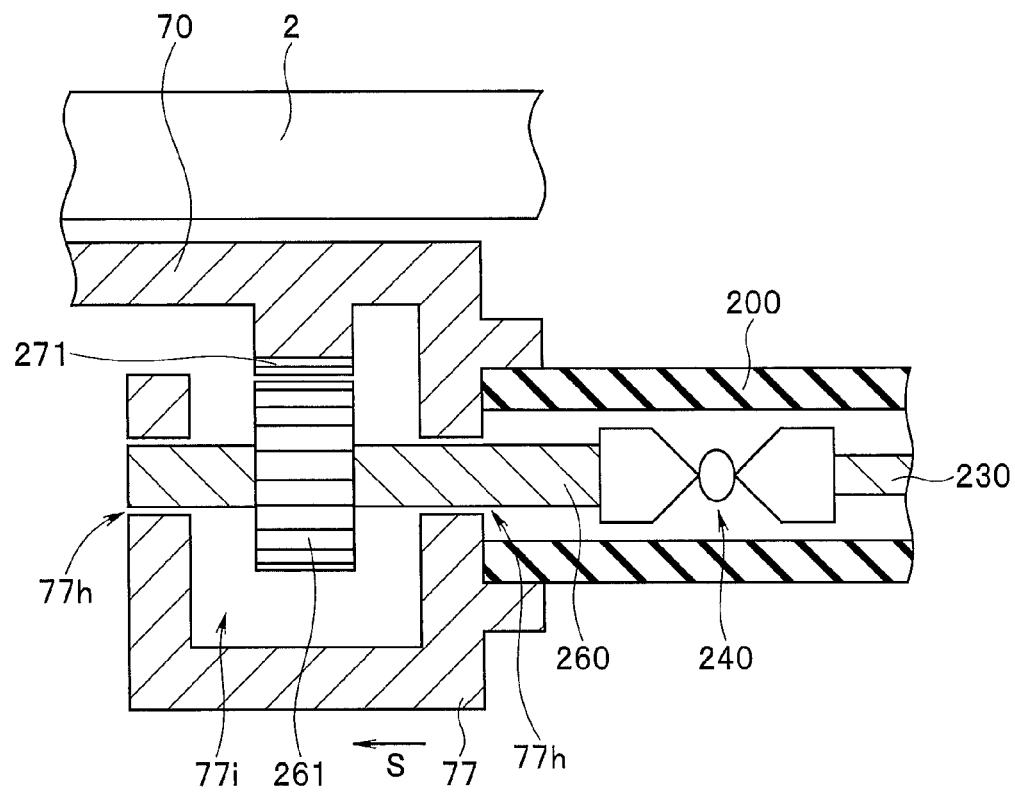
FIG. 19 is a partial sectional view showing part of a drive mechanism of the rotation body of FIG. 18 under enlargement.

FIG. 18 is a view schematically showing a configuration in which a cover sheath with a flexible shaft that supplies a rotational force to a rotation body that is put on the outer periphery of the insertion portion of the endoscope being inserted through an inside thereof, and the insertion portion are connected with a clip. FIG. 19 is a partial sectional view showing part of a drive mechanism of the rotation body of FIG. 18 under enlargement.

Incidentally, the art of enhancing insertability of the insertion portion by the screw action using contact of a rotation body and a body cavity wall by the outer periphery of the insertion portion of the endoscope being covered with the rotation body provided with a spiral fin portion, and the rotation body being rotated with respect to the insertion portion is known.

In the endoscope system having the configuration as above, the configuration is known, which transmits the rotational force from the motor that is provided in the insertion portion or the operation portion of the endoscope to the rotation body.

However, if the motor is provided in the insertion portion or the operation portion of the endoscope, the problem arises, that the insertion portion or the operation portion cannot be cleaned and disinfected unless the motor is detached from the insertion portion or the operation portion.

Thus, as shown in FIG. 18, in the present configuration, a motor 221 is provided outside the insertion portion 2 and the operation portion 3, more specifically, a control apparatus for the motor that is an external apparatus of the endoscope, or a connection connector of the endoscope to the external apparatus. Note that the motor 221 may be externally attached to or contained in the control apparatus. Further, the motor 221 is fixed to the connection connector by being externally attached thereto.

More specifically, as shown in FIG. 18 and FIG. 19, a distal end of an elongated cover sheath 200 that is extended from the motor 221 is attachable to and detachable from the rotation body 70. Further, in the cover sheath 200, a flexible shaft 230 that is rotated by drive of the motor 221 is provided.

Further, in a connection portion 77 that is provided at a proximal end of the rotation body 70 and is extended outward in a radial direction, a hole 77h that penetrates in the insertion direction is formed. Further, in a clearance 77i in the connection portion 77, a flexible shaft 260 is pivotally supported rotatably with respect to the hole 77h.

The flexible shaft 260 is provided with a gear 261 that rotates with the flexible shaft 260, in the clearance 77i in the connection portion 77, and the gear 261 is meshed with a gear 271 provided at the outer periphery of the rotation body 70.

Further, a distal end that is extended to the rear side from clearance 77i, of the flexible shaft 260 is attachable to and detachable from the flexible shaft 230 by a universal joint 240, in the cover sheath 200.

Namely, the configuration is such that when the distal end of the cover sheath 200 is connected to the proximal end of the rotation body 70, a proximal end of the flexible shaft 260 is connected to a distal end of the flexible shaft 230 by the universal joint 240, in the cover sheath 200.

In the configuration as above, when the motor 221 is driven, the rotation body 70 rotates via the flexible shafts 230 and 260, and the gears 261 and 271.

According to the configuration as above, the motor 221 is provided at a position away from the insertion portion 2 and the operation portion 3, and therefore, cleaning and disinfecting of the insertion portion 2 and the operation portion 3 can be reliably performed.

Further, when the cover sheath 200 sags in the configuration using the elongated cover sheath 200, the flexible shaft 230 rotates while the flexible shaft 230 is swinging in the radial direction of the cover sheath 200 in the cover sheath 200 when the flexible shaft 230 that is inserted through the inside of the cover sheath 200 rotates, and therefore, the problem arises, that the cover sheath 200 also swings. Further, since the cover sheath 200 is formed to be elongated, the problem also arises, that the cover sheath 200 easily contacts other members.

Thus, as shown in FIG. 18, the present configuration adopts a configuration that fixes the cover sheath 200 to the outer periphery of the insertion portion 2 by using a clip member 250.

According to the configuration as above, the cover sheath 200 does not sag, and in addition, contact of the cover sheath 200 to the other members can be effectively prevented.

What is claimed is:

1. An endoscope system, comprising:
    an insertion portion that is inserted into a subject;
    a function portion that is provided at the insertion portion and is capable of acting;
    an operation portion that is connected to the insertion portion;
    a universal cord that has a distal end, a proximal end and a drive force transmitting member, the distal end being connected to the operation portion, the proximal end having a connection connector to be connected to an external apparatus, the drive force transmitting member being arranged inside the universal cord for transmitting a drive force for operating the function portion from the proximal end to the distal end;
    a control apparatus that outputs a control signal for generating the drive force; and
    a drive cable having a distal end, a proximal end and a motor, the distal end of the drive cable being connected to the connection connector, the proximal end of the drive cable being connected to the control apparatus, the motor being driven by receiving the control signal from the proximal end of the drive cable, and inputting the drive force from the distal end of the drive cable to the connection connector.

2. The endoscope system according to claim 1, wherein the motor being positioned at the distal end of the drive cable.

3. The endoscope system according to claim 1, wherein the drive force transmitting member is a flexible shaft that gives the drive force to the function portion by rotation, and
    the flexible shaft is capable of being given a rotational force from the motor, when the drive cable is connected to the connection connector and the control apparatus.

4. The endoscope system according to claim 1, wherein the function portion is a bending portion that is provided at the insertion portion, and is electrically caused to bend by being given the drive force from the motor.

5. The endoscope system according to claim 1, wherein the function portion has a rotation body that is put on an outer periphery of the insertion portion, electrically rotates by being given the drive force from the motor, and propels the insertion portion into the subject.

6. The endoscope system according to claim. 1, wherein the connection portion has a bevel gear at the proximal end of the drive force transmitting member for transferring the drive force from the motor to the drive force transmitting member.

* * * * *